(12) United States Patent
Reed et al.

(10) Patent No.: US 7,638,324 B2
(45) Date of Patent: Dec. 29, 2009

(54) BCL-G POLYPEPTIDES, ENCODING NUCLEIC ACIDS AND METHODS OF USE

(75) Inventors: John C. Reed, Rancho Santa Fe, CA (US); Adam Godzik, San Diego, CA (US); Bin Guo, San Diego, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 507 days.

(21) Appl. No.: 09/738,396

(22) Filed: Dec. 14, 2000

(65) Prior Publication Data

US 2001/0029013 A1 Oct. 11, 2001

Related U.S. Application Data

(60) Provisional application No. 60/287,581, filed on Dec. 14, 1999.

(51) Int. Cl.
| C07H 21/02 | (2006.01) |
| C07H 21/04 | (2006.01) |
| C12Q 1/68 | (2006.01) |
| C12N 5/00 | (2006.01) |
| A61K 31/70 | (2006.01) |

(52) U.S. Cl. ................ 435/325; 435/6; 435/69.1; 435/320.1; 435/252.3; 536/23.1; 536/24.1; 536/24.3; 536/24.33; 536/24.5

(58) Field of Classification Search ........................ None
See application file for complete search history.

(56) References Cited

U.S. PATENT DOCUMENTS

| 5,616,491 A | 4/1997 | Mak et al. |
| 5,691,179 A | 11/1997 | Korsmeyer |
| 5,750,826 A | 5/1998 | Borkowski et al. |
| 5,981,830 A | 11/1999 | Wu et al. |

FOREIGN PATENT DOCUMENTS

| WO | WO95/00642 | 1/1995 |
| WO | WO95/28497 | 10/1995 |
| WO | WO97/45128 | 12/1997 |

OTHER PUBLICATIONS

Guo et al., "Bcl-G, a novel pro-apoptotic member of the Bcl-2 family," *J. Biol. Chem.* 276(4):2780-2785 (2001).
Adams and Cory, "The Bcl-2 protein family: arbiters of cell survival," *Science* 281:1322-1326 (1998).
Aissani et al., "Childhood Acute Lymphoblastic Leukemia: Is There a Tumor Suppressor Gene in Chromosome 12p12.3?" *Leuk. Lymphoma*, 34:231-239 (1999).
Altschul et al., "Gapped BLAST and PSI-BLAST: a new generation of protein database search programs," *Nucleic Acids Res.* 25:3389-3402 (1997).
Altschul et al., "Basic local alignment search tool," *J. Mol. Biol.* 215:403-410 (1990).
Angeles et al., "Mutations in the voltage-dependent anion channel of the mitochondrial outer membrane cause a dominant nonlethal growth impairment," *J. Bioenerg. Biomembr.* 2:143-151 (1999).
Antonsson et al., "Inhibition of Bax channel-forming activity by Bcl-2," *Science* 277:370-372 (1997).
Baccichet and Sinnett, "Frequent deletion of chromosome 12p12.3 in children with acute lymphoblastic leukaemia," *Br. J. Haematol.*, 99:107-114 (1997).
Baens et al., "A Physical Transcript, and Deletion Map of Chromosome Region 12p12.3 Flanked by ETV6 and CDKN1B: Hypermethylation of the LRP6 CpG Island in Two Leukemia Patients with Hemizygous del (12p)," *Genomics*, 56:40-50 (1999).
Bingle et al., "Exon skipping in Mcl-1 results in a bcl-2 homology domain 3 only gene product that promotes cell death," *J. Biol. Chem.* 275:22136-22146 (2000).
Boise et al., "bcl-x, a bcl-2-related gene that functions as a dominant regulator of apoptotic cell death," *Cell* 74:597-608 (1993).
Bouillet et al., "Proapoptotic Bcl-2 relative Bim required for certain apoptotic responses, leukocyte homeostasis, and to preclude autoimmunity," *Science* 286:1735-1738 (1999).
Burcin et al., "Adenovirus-mediated regulable target gene expression in vivo," *Proc. Natl. Acad. Sci. USA*, 96:355-360 (1999).
Capecchi M., "Altering the genome by homologous recombination," *Science* 244:1288-1292 (1989).
Crompton M., "The mitochondrial permeability transition pore and its role in cell death," *Biochem J.* 341:233-249 (1999).
Datta et al., "Cellular survival: a play in three Akts," *Genes & Dev.* 13:2905-2927 (1999).
Dolder et al., "Crystallization of the human, mitochondrial voltage-dependent anion-selective channel in the presence of phospholipids," *J. Struct. Biol.* 127:64-71 (1999).
Ellerby et al., "Anti-cancer activity of targeted pro-apoptotic peptides," *Nature Medicine*, 5:1032-1038 (1999).

(Continued)

*Primary Examiner*—Sean R McGarry
(74) *Attorney, Agent, or Firm*—McDermott Will & Emery LLP

(57) ABSTRACT

The invention provides Bcl-G polypeptides and encoding nucleic acids. Bcl-G polypeptides include Bcl-$G_L$ and Bcl-$G_S$. The invention also provides mouse Bcl-G. The invention also provides vectors containing Bcl-G nucleic acids, host cells containing such vectors, Bcl-G anti-sense nucleic acids and related compositions. The invention additionally provides Bcl-G oligonucleotides that can be used to hybridize to or amplify a Bcl-G nucleic acid. Anti-Bcl-G specific antibodies are also provided. Further provided are kits containing Bcl-G nucleic acids or Bcl-G specific antibodies. Such kits and reagents can be used to diagnose cancer, monitor response to therapy, or predict the prognosis of a cancer patient. The invention additionally provides methods of modulating apoptosis using Bcl-G polypeptides, encoding nucleic acids, or compounds that modulate the activity or expression of Bcl-G polypeptides. The methods for modulating apoptosis can be used to treat diseases such as cancer.

65 Claims, 11 Drawing Sheets

OTHER PUBLICATIONS

Green and Reed, "Mitochondria and Apoptosis," *Science*, 281:1309-1312 (1998).

Gross et al., "BCL-2 family members and the mitochondria in apoptosis," *Genes Dev.* 13:1899-1911 (1999).

Hatta et al., "Ovarian cancer has frequent loss of heterozygosity at chromosome 12p12.3-13.1 (region of TEL and Kipl loci) and chromosome 12q23-ter: evidence for two new tumour-supressor genes," *Br. J. Cancer*, 75:1256-1262 (1997).

Heermeier et al., "Bax and Bcl-xs are induced at the onset of apoptosis in involuting mammary epithelial cells," *Mech. Dev.* 56:197-207 (1996).

Holinger et al., "Bak BH3 Peptides Antagonize Bcl-$x_L$ Function and Induce Apoptosis through Cytochrome *c*-independent Activation of Caspases," *J. Biol. Chem.*, 274:13298-13304 (1999).

Kelekar et al., "Bad is a BH3 domain-containing protein that forms an inactivating dimer with Bcl-$x_L$," *Mol. Cell. Biol.* 17:7040-7046 (1997).

Kelekar and Thompson, "Bcl-2-family proteins: the role of the BH3 domain in apoptosis," *Trends Cell Biol.* 8:324-330 (1998).

Kibel et al., "Identification of 12p as a region of frequent deletion in advanced prostate cancer," *Cancer Res.*, 58:5652-5655 (1998).

Kibel et al., "Loss of heterozygosity at 12P12-13 in primary and metastatic prostate adena," *J. Urol.* 164:192-196 (2000).

Knudson et al., "Bax-deficient mice with lymphoid hyperplasia and male germ cell death," *Science* 270:96-99 (1995).

Kroemer and Reed, "Mitochondrial control of cell death," *Nature Med.* 6:513-519 (2000).

Li et al., "Cleavage of Bid by caspase 8 mediates the mitochondrial damage in the Fas pathway of apoptosis," *Cell* 94:491-501 (1998).

Luo et al., "Bid, a Bcl2 interacting protein, mediates cytochrome c release from mitochondria in response to activation of cell surface death receptors," *Cell* 94:481-490 (1998).

Matsuyama et al., "The Mitochondrial $F_0F_1$-ATPase Proton Pump in Required for Function of the Proapoptotic Protein Bax in Yeast and Mammalian Cells," *Molecular Cell*, 1:327-336 (1998).

Motoyama et al., "Massive cell death of immature hematopoietic cells and neurons in Bcl-x-deficient mice," *Science* 267:1506-1510 (1995).

O'Connor et al., "Bim: a novel member of the Bcl-2 family that promotes apoptosis," *EMBO J.* 17:384-395 (1998).

Oltvai et al., "Bcl-2 heterodimerizes in vivo with a conserved homolog, Bax, that accelerates programmed cell death," *Cell* 74:609-619 (1993).

Ottilie et al., "Dimerization properties of human BAD," *J. Biol. Chem.* 272:30866-30872 (1997).

Priault et al., "Comparison of the effects of bax-expression in yeast under fermentative and respiratory conditions: investigation of the role of adenine nucleotides carrier and cytochrome c.," *FEBS Lett.*, 456:232-238 (1999).

Puthalakath et al., "The proapoptotic activity of the Bcl-2 family member Bim is regulated by interaction with the dynein motor complex," *Mol. Cell.* 3:287-296 (1999).

Reed J., "Bcl-2 Family Proteins," *Oncogene*, 17:3225-3236 (1998).

Reed J., "Mechanisms of apoptosis avoidance in cancer," *Curr. Opin. Oncology*, 11:68-75 (1999).

Reed J., "Double-identity for proteins of the Bcl-2 family," *Nature*, 387:773-776 (1997).

Rohl et al., "The outer envelope protein OEP24 from pea chloroplasts can functionally replace the mitochondrial VDAC in yeast," *FEBS Lett.*, 460:491-494 (1999).

Sattler et al, "Structure of Bcl-$x_L$-Bak peptide complex: recognition between regulators of apoptosis," *Science* 275:983-986 (1997).

Schendel et al., "Bcl-2 family proteins as ion-channels," *Cell Death Differ.* 5:372-380 (1998).

Schlesinger et al., "Comparison of the ion channel characteristics of proapoptotic BAX and antiapoptotic BCL-2," *Proc. Natl. Acad. Sci. USA* 94:11357-11362 (1997).

Schwarze et al., "In Vivo Protein Transduction: Delivery of a Biologically Active Protein into the Mouse," *Science*, 285:1569-1572 (1999).

Shastry B, "Gene disruption in mice: models of development and disease," *Mol. Cell. Biochem.* 181:163-179 (1998).

Shastry B, "Genetic knockouts in mice: an update," *Experentia* 51:1028-1039 (1995).

Shimizu et al., "Electrophysiological study of a novel large pore formed by Bax and the voltage-dependent anion channel that is permeable to cytochrome c," *J. Biol. Chem.* 16:12321-12325 (2000).

Tao et al., "Bcl-xS and Bad Potentiate the Death Suppressing Activities of Bcl-xL, Bcl-2, and A1 in Yeast," *J. Biol. Chem.*, 273:23704-23708 (1998).

Tatusova and Madden, "BLAST 2 sequences, a new tool for comparing protein and nucleotide sequences," *FEMS Microbiol Lett.* 174:247-250 (1999).

Tsujimoto and Croce, "Analysis of the structure, transcripts, and protein products of *bcl-2*, the gene involved in human follicular lymphoma," *Proc. Natl. Acad. Sci. USA* 83:5214-5218 (1986).

Veis et al., "Bcl-2-deficient mice demonstrate fulminant lymphoid apoptosis, polycystic kidneys, and hypopigmented hair," *Cell* 75:229-240 (1993).

Vocero-Akbani et al., "Killing HIV-infected cells by transduction with an HIV protease-activated caspase-3 protein," *Nature Medicine*, 5:29-33 (1999).

Wang et al., "Mutagenesis of the BH3 domain of BAX identifies residues critical for dimerization and killing," *Mol. Cell. Biol.* 18:6083-6089 (1998).

Wolter et al., "Movement of BAX from the cytosol to mitochondria during apoptosis," *J. Cell Biol.* 139:1281-1292 (1997).

Xu and Reed, "Bax inhibitor-1, a mammalian apoptosis suppressor identified by functional screening in yeast," *Mol. Cell* 1:337-346 (1998).

Yang et al., "Bad, a heterodimeric partner for Bcl-$X_L$ and Bcl-2, displaces Bax and promotes cell death," *Cell* 80:285-291 (1995).

Ye et al., "Regulated Delivery of Therapeutic Proteins After in Vivo Somatic Cell Gene Transfer," *Science*, 283:88-91 (1999).

Yin et al, "Bid-deficient mice are resistant to Fas-induced hepatocellular apoptosis," *Nature* 400:886-891 (1999).

Zha et al., "BH3 domain of Bad is required for heterodimerization with Bcl-$X_L$ and pro-apoptotic activity," *J. Biol. Chem.* 272:24101-24104 (1997).

Zha et al., "Structure-function comparisons of the proapoptotic protein Bax in yeast and mammalian cells," *Mol. Cell. Biol.* 16:6494-6508 (1996).

Zhang et al., "Bar: An apoptosis regulator at the intersection of caspases and Bcl-2 family proteins," *Proc. Natl. Acad. Sci. USA* 97:2597-2602 (2000).

Zimmer and Gruss, "Production of chimaeric mice containing embryonic stem (ES) cells carrying a homoeobox *Hox 1.1* allele mutated by homologous recombination," *Nature* 338:150-153 (1989).

```
         10        20        30        40
    |....|....|....|....|....|....|....|....|
aatgacatgacagccattccgtggccaggccaaccactgc   40
ccaagctggagaccacgaggattcagggactgaagccagc   80
atgggaattcctggtttgagatcagagtcctgagtacctc  120
gtgggaacttggcactcatccgcaggaggtctagacccc   160
cagagaattccttgagtctaaggcacaggccaacatgtg   200
        210       220       230       240
    |....|....|....|....|....|....|....|....|
tagcaccagtgggtgtgacctggaagaaatcccctagat   240
gatgatgacctaaacaccatagaattcaaaatcctcgcct  280
actacaccagacatcatgtcttcaagagcacccctgctct  320
cttctcaccaaagctgctgagaacaagaagtttgtcccag  360
aggggcctggggaattgttcgcaaatgagtcatggacag   400
        410       420       430       440
    |....|....|....|....|....|....|....|....|
aggtgtcatggccttgcagaaattcccaatccagtgagaa  440
ggccataaaccttggcaagaaaaagtcttcttggaaagca  480
ttctttggagtagtggagaaggaagattcgcagagcacgc  520
ctgccaaggtctctgctcagggtcaaaggacgttggaata  560
ccaagattcgcacagccagcagtggtccaggtgtctttct  600
        610       620       630       640
    |....|....|....|....|....|....|....|....|
aacgtggagcagtgcttggagcatgaagctgtggacccca  640
aagtcatttccattgccaaccgagtagctgaaattgttta  680
ctcctggccaccaccacaagcgacccaggcaggaggcttc  720
aagtccaaagagattttttgtaactgagggtctctccttcc  760
agctccaaggccacgtgcctgtagcttcaagttctaagaa  800
        810       820       830       840
    |....|....|....|....|....|....|....|....|
agatgaagaagaacaaatactagccaaaattgttgagctg  840
ctgaaatattcaggagatcagttggaaagaaagctgaaga  880
aagataaggctttgatgggccacttccaggatgggctgtc  920
ctactctgttttcaagaccatcacagaccaggtcctaatg  960
ggtgtggaccccaggggagaatcagaggtcaaagctcagg  1000
       1010      1020      1030      1040
    |....|....|....|....|....|....|....|....|
gctttaaggctgcccttgtaatagacgtcacggccaagct  1040
cacagctattgacaaccacccgatgaacagggtcctgggc  1080
tttggcaccaagtacctgaaagagaacttctcgccatgga  1120
tccagcagcacggtggatgggaaaaaatacttgggatatc  1160
acatgaagaagtagactga  1179
```

FIGURE 1

Bcl-G_L

```
  1 - ATGTGTAGCACCAGTGGGTGTGACCTGGAAGAAATCCCCCTAGATGATGATGACCTAAAC -  60
    - M  C  S  T  S  G  C  D  L  E  E  I  P  L  D  D  D  D  L  N
 61 - ACCATAGAATTCAAAATCCTCGCCTACTACACCAGACATCATGTCTTCAAGAGCACCCCT - 120
    - T  I  E  F  K  I  L  A  Y  Y  T  R  H  H  V  F  K  S  T  P
121 - GCTCTCTTCTCACCAAAGCTGCTGAGAACAAGAAGTTTGTCCCAGAGGGGCCTGGGAAT - 180
    - A  L  F  S  P  K  L  L  R  T  R  S  L  S  Q  R  G  L  G  N
181 - TGTTCAGCAAATGAGTCATGGACAGAGGTGTCATGGCCTTGCAGAAATTCCCAATCCAGT - 240
    - C  S  A  N  E  S  W  T  E  V  S  W  P  C  R  N  S  Q  S  S
241 - GAGAAGGCCATAAACCTTGGCAAGAAAAAGTCTTCTTGGAAAGCATTCTTTGGAGTAGTG - 300
    - E  K  A  I  N  L  G  K  K  K  S  S  W  K  A  F  F  G  V  V
301 - GAGAAGGAAGATTCGCAGAGCACGGCCTGCCAAGGTCTCTGCTCAGGGTCAAAGGACGTTG - 360
    - E  K  E  D  S  Q  S  T  P  A  K  V  S  A  Q  G  Q  R  T  L
361 - GAATACCAAGATTCGCACAGCCAGCAGTGGTCCAGGTGTCTTTCTAACGTGGAGCAGTGC - 420
    - E  Y  Q  D  S  H  S  Q  Q  W  S  R  C  L  S  N  V  E  Q  C
421 - TTGGAGCATGAAGCTGTGGACCCCAAAGTCATTTCCATTGCCAACCGAGTAGCTGAAATT - 480
    - L  E  H  E  A  V  D  P  K  V  I  S  I  A  N  R  V  A  E  I
481 - GTTTACTCCTGGCCACCACCACAAGCGACCCAGGCAGGAGGCTTCAAGTCCAAAGAGATT - 540
    - V  Y  S  W  P  P  P  Q  A  T  Q  A  G  G  F  K  S  K  E  I
541 - TTTGTAACTGAGGGTCTCTCCTTCCAGCTCCAAGGCCACGTGCCTGTAGCTTCAAGTTCT - 600
    - F  V  T  E  G  L  S  F  Q  L  Q  G  H  V  P  V  A  S  S  S
601 - AAGAAAGATGAAGAAGAACAAATACTAGCCAAAATTGTTGAGCTGCTGAAATATTCAGGA - 660
    - K  K  D  E  E  E  Q  I  L  A  K  I  V  E  L  L  K  Y  S  G
661 - GATCAGTTGGAAAGAAAGCTGAAGAAAGATAAGGCTTTGATGGGCCACTTCCAGGATGGG - 720
    - D  Q  L  E  R  K  L  K  K  D  K  A  L  M  G  H  F  Q  D  G
721 - CTGTCCTACTCTGTTTTTCAAGACCATCACAGACCAGGTCCTAATGGGTGTGGACCCCAGG - 780
    - L  S  Y  S  V  F  K  T  I  T  D  Q  V  L  M  G  V  D  P  R
781 - GGAGAATCAGAGGTCAAAGCTCAGGGCTTTAAGGCTGCCCTTGTAATAGACGTCACGGCC - 840
    - G  E  S  E  V  K  A  Q  G  F  K  A  A  L  V  I  D  V  T  A
841 - AAGCTCACAGCTATTGACAACCACCCGATGAACAGGGTCCTGGGCTTTGGCACCAAGTAC - 900
    - K  L  T  A  I  D  N  H  P  M  N  R  V  L  G  F  G  T  K  Y
901 - CTGAAAGAGAACTTCTCGCCATGGATCCAGCAGCACGGTGGATGGAAAAAATACTTGGG - 960
    - L  K  E  N  F  S  P  W  I  Q  Q  H  G  G  W  E  K  I  L  G
961 - ATATCACATGAAGAAGTAGACTGA - 984
    - I  S  H  E  E  V  D  *
```

FIGURE 2

```
          10        20        30        40
   ....|....|....|....|....|....|....|....|
   aatgacatgacagccattccgtggccagggacaccactgc  40
   ccaagctggagaccacgaggattcagggactgaagccagc  80
   atgggaattcctggtttgagatcagagtcctgagtacctc 120
   gtgggaacttgggcactcatccgcaggaggtctagacccc 160
   cagagaattccttgagtctaaggcacaggcccaacatgtg 200
         210       220       230       240
   ....|....|....|....|....|....|....|....|
   tagcaccagtgggtgtgacctggaagaaatcccctagat  240
   gatgatgacctaaacaccatagaattcaaaatcctcgcct 280
   actacaccagacatcatgtcttcaagagcaccctgctct  320
   cttctcaccaaagctgctgagaacaagaagtttgtcccag 360
   aggggcctggggaattgttcagcaaatgagtcatggacag 400
         410       420       430       440
   ....|....|....|....|....|....|....|....|
   aggtgtcatggccttgcagaaattcccaatccagtgagaa 440
   ggccataaaccttggcaagaaaagtcttcttggaaagca  480
   ttctttggagtagtggagaaggaagattcgcagagcacgc 520
   ctgccaaggtctctgctcagggtcaaaggacgttggaata 560
   ccaagattcgcacagccagcagtggtccaggtgtctttct 600
         610       620       630       640
   ....|....|....|....|....|....|....|....|
   aacgtggagcagtgcttggagcatgaagctgtggacccca 640
   aagtcatttccattgccaaccgagtagctgaaattgttta 680
   ctcctggccaccaccacaagcgacccaggcaggaggcttc 720
   aagtccaaagagattttttgtaactgagggtctctccttcc 760
   agctccaaggccacgtgcctgtagcttcaagttctaagaa 800
         810       820       830       840
   ....|....|....|....|....|....|....|....|
   agatgaagaagaacaaatactagccaaaattgttgagctg 840
   ctgaaatattcaggagatcagttggaaagaaaggacactg 880
   ccttcatccccattcccttggttgacaccagcatccaggg 920
   ttttccacaggatggtttgatggcctgcatttga        954
```

FIGURE 3

Bcl-G_S

```
  1 - ATGTGTAGCACCAGTGGGTGTGACCTGGAAGAAATCCCCTAGATGATGATGACCTAAAC -  60
    - M   C   S   T   S   G   C   D   L   E   E   I   P   L   D   D   D   D   L   N
 61 - ACCATAGAATTCAAAATCCTCGCCTACTACACCAGACATCATGTCTTCAAGAGCACCCCT - 120
    - T   I   E   F   K   I   L   A   Y   Y   T   R   H   H   V   F   K   S   T   P
121 - GCTCTCTTCTCACCAAAGCTGCTGAGAACAAGAAGTTTGTCCCAGAGGGGCCTGGGAAT - 180
    - A   L   F   S   P   K   L   L   R   T   R   S   L   S   Q   R   G   L   G   N
181 - TGTTCAGCAAATGAGTGGACAGAGGTGTCATGGCCTTGCAGAAATTCCCAATCCAGT - 240
    - C   S   A   N   E   S   W   T   E   V   S   W   P   C   R   N   S   Q   S   S
241 - GAGAAGGGCCATAAACCTGGCAAGAAAAAGTCTTCTTGGAAAGCATTCTTTGGAGTAGTG - 300
    - E   K   A   I   N   L   G   K   K   K   S   S   W   K   A   F   F   G   V   V
301 - GAGAAGGAAGATTCGCAGAGCACGCCTGCCAAGGTCTCTGCTCAGGGTCAAAGGACGTTG - 360
    - E   K   E   D   S   Q   S   T   P   A   K   V   S   A   Q   G   R   T   L
361 - GAATACCAAGATTCGCACAGCAGTGTCCAGTGGTCTCTTTCTAACGTGGAGCAGTGC - 420
    - E   Y   Q   D   S   H   S   Q   Q   W   S   R   C   L   S   N   V   E   Q   C
421 - TTGGAGCATGAAGCTGTGGACCCCAAAGTCATTTCCATTGCCAACCGAGTAGCTGAAATT - 480
    - L   E   H   E   A   V   D   P   K   V   I   S   I   A   N   R   V   A   E   I
481 - GTTTACTCCTGGCCACCACCACCAAGCGACCCAGGAGGCTTCAAGTCCAAAGAGATT - 540
    - V   Y   S   W   P   P   P   Q   A   T   Q   A   G   G   F   K   S   K   E   I
541 - TTTGTAACTGAGGGTCTCTCCTTCCAGCTCCAAGGCCACGTGCCTGTAGCTTCAAGTTCT - 600
    - F   V   T   E   G   L   S   F   Q   L   Q   G   H   V   P   V   A   S   S
601 - AAGAAAGATGAAGAAGAACAAATACTAGCCAAAATTGTTGAGCTGCTGAAATATTCAGGA - 660
    - K   K   D   E   E   E   Q   I   L   A   K   I   V   E   L   L   K   Y   S   G
661 - GATCAGTTGGAAAGAAAGGACACTGCCTTCATCCCCATTCCCCTTGGTTGACACCAGCATC - 720
    - D   Q   L   E   R   K   D   T   A   F   I   P   I   P   L   V   D   T   S   I
721 - CAGGGTTTTCCACAGGATGGTTTGATGGCCTGCATTTGA         - 759
    - Q   G   F   P   Q   D   G   L   M   A   C   I   *
```

FIGURE 4

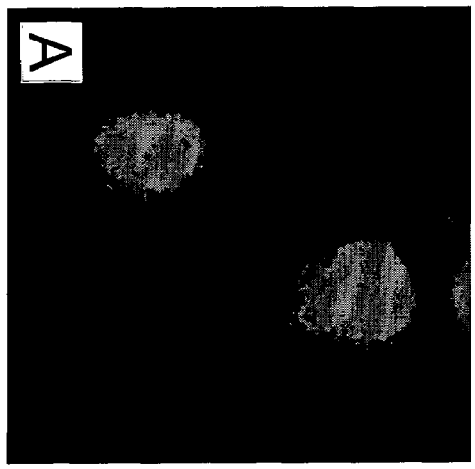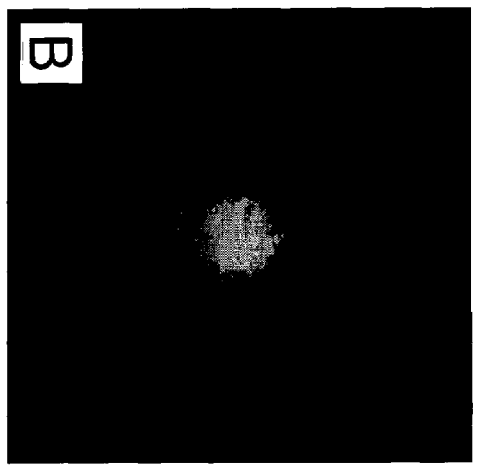
FIGURE 11

SEQUENCE LISTING

<160> NUMBER OF SEQ ID NOS: 44

<210> SEQ ID NO 1
<211> LENGTH: 1179
<212> TYPE: DNA
<213> ORGANISM: Homo sapiens
<220> FEATURE:
<221> NAME/KEY: CDS
<222> LOCATION: (196)..(1179)

<400> SEQUENCE: 1

```
aatgacatga cagccattcc gtggccaggg acaccactgc ccaagctgga gaccacgagg        60
attcagggac tgaagccagc atgggaattc ctggtttgag atcagagtcc tgagtacctc       120
gtgggaactt gggcactcat ccgcaggagg tctagacccc cagagaattc cttgagtcta       180
aggcacaggc ccaac atg tgt agc acc agt ggg tgt gac ctg gaa gaa atc        231
               Met Cys Ser Thr Ser Gly Cys Asp Leu Glu Glu Ile
                 1               5                  10 ccc cta gat gat gat gac cta aac acc ata gaa ttc aaa atc ctc gcc         279
Pro Leu Asp Asp Asp Asp Leu Asn Thr Ile Glu Phe Lys Ile Leu Ala
            15                  20                  25 tac tac acc aga cat cat gtc ttc aag agc acc cct gct ctc ttc tca         327
Tyr Tyr Thr Arg His His Val Phe Lys Ser Thr Pro Ala Leu Phe Ser
     30                  35                  40 cca aag ctg ctg aga aca aga agt ttg tcc cag agg ggc ctg ggg aat         375
Pro Lys Leu Leu Arg Thr Arg Ser Leu Ser Gln Arg Gly Leu Gly Asn
 45                  50                  55                  60 tgt tca gca aat gag tca tgg aca gag gtg tca tgg cct tgc aga aat         423
Cys Ser Ala Asn Glu Ser Trp Thr Glu Val Ser Trp Pro Cys Arg Asn
                 65                  70                  75 tcc caa tcc agt gag aag gcc ata aac ctt ggc aag aaa aag tct tct         471
Ser Gln Ser Ser Glu Lys Ala Ile Asn Leu Gly Lys Lys Lys Ser Ser
             80                  85                  90 tgg aaa gca ttc ttt gga gta gtg gag aag gaa gat tcg cag agc acg         519
Trp Lys Ala Phe Phe Gly Val Val Glu Lys Glu Asp Ser Gln Ser Thr
         95                 100                 105 cct gcc aag gtc tct gct cag ggt caa agg acg ttg gaa tac caa gat         567
Pro Ala Lys Val Ser Ala Gln Gly Gln Arg Thr Leu Glu Tyr Gln Asp
    110                 115                 120 tcg cac agc cag cag tgg tcc agg tgt ctt tct aac gtg gag cag tgc         615
Ser His Ser Gln Gln Trp Ser Arg Cys Leu Ser Asn Val Glu Gln Cys
125                 130                 135                 140 ttg gag cat gaa gct gtg gac ccc aaa gtc att tcc att gcc aac cga         663
Leu Glu His Glu Ala Val Asp Pro Lys Val Ile Ser Ile Ala Asn Arg
                145                 150                 155 gta gct gaa att gtt tac tcc tgg cca cca cca caa gcg acc cag gca         711
Val Ala Glu Ile Val Tyr Ser Trp Pro Pro Pro Gln Ala Thr Gln Ala
            160                 165                 170 gga ggc ttc aag tcc aaa gag att ttt gta act gag ggt ctc tcc ttc         759
Gly Gly Phe Lys Ser Lys Glu Ile Phe Val Thr Glu Gly Leu Ser Phe
        175                 180                 185 cag ctc caa ggc cac gtg cct gta gct tca agt tct aag aaa gat gaa         807
Gln Leu Gln Gly His Val Pro Val Ala Ser Ser Ser Lys Lys Asp Glu
    190                 195                 200 gaa gaa caa ata cta gcc aaa att gtt gag ctg ctg aaa tat tca gga         855
Glu Glu Gln Ile Leu Ala Lys Ile Val Glu Leu Leu Lys Tyr Ser Gly
205                 210                 215                 220 gat cag ttg gaa aga aag ctg aag aaa gat aag gct ttg atg ggc cac         903
Asp Gln Leu Glu Arg Lys Leu Lys Lys Asp Lys Ala Leu Met Gly His
```

```
                  225                 230                 235
ttc cag gat ggg ctg tcc tac tct gtt ttc aag acc atc aca gac cag      951
Phe Gln Asp Gly Leu Ser Tyr Ser Val Phe Lys Thr Ile Thr Asp Gln
                240                 245                 250 gtc cta atg ggt gtg gac ccc agg gga gaa tca gag gtc aaa gct cag      999
Val Leu Met Gly Val Asp Pro Arg Gly Glu Ser Glu Val Lys Ala Gln
            255                 260                 265 ggc ttt aag gct gcc ctt gta ata gac gtc acg gcc aag ctc aca gct     1047
Gly Phe Lys Ala Ala Leu Val Ile Asp Val Thr Ala Lys Leu Thr Ala
        270                 275                 280 att gac aac cac ccg atg aac agg gtc ctg ggc ttt ggc acc aag tac     1095
Ile Asp Asn His Pro Met Asn Arg Val Leu Gly Phe Gly Thr Lys Tyr
285                 290                 295                 300 ctg aaa gag aac ttc tcg cca tgg atc cag cag cac ggt gga tgg gaa     1143
Leu Lys Glu Asn Phe Ser Pro Trp Ile Gln Gln His Gly Gly Trp Glu
                305                 310                 315 aaa ata ctt ggg ata tca cat gaa gaa gta gac tga                     1179
Lys Ile Leu Gly Ile Ser His Glu Glu Val Asp
                320                 325

<210> SEQ ID NO 2
<211> LENGTH: 327
<212> TYPE: PRT
<213> ORGANISM: Homo sapiens

<400> SEQUENCE: 2

Met Cys Ser Thr Ser Gly Cys Asp Leu Glu Glu Ile Pro Leu Asp Asp
 1               5                   10                  15

Asp Asp Leu Asn Thr Ile Glu Phe Lys Ile Leu Ala Tyr Tyr Thr Arg
            20                  25                  30

His His Val Phe Lys Ser Thr Pro Ala Leu Phe Ser Pro Lys Leu Leu
        35                  40                  45

Arg Thr Arg Ser Leu Ser Gln Arg Gly Leu Gly Asn Cys Ser Ala Asn
    50                  55                  60

Glu Ser Trp Thr Glu Val Ser Trp Pro Cys Arg Asn Ser Gln Ser Ser
65                  70                  75                  80

Glu Lys Ala Ile Asn Leu Gly Lys Lys Ser Ser Trp Lys Ala Phe
                85                  90                  95

Phe Gly Val Val Glu Lys Glu Asp Ser Gln Ser Thr Pro Ala Lys Val
            100                 105                 110

Ser Ala Gln Gly Gln Arg Thr Leu Glu Tyr Gln Asp Ser His Ser Gln
        115                 120                 125

Gln Trp Ser Arg Cys Leu Ser Asn Val Glu Gln Cys Leu Glu His Glu
    130                 135                 140

Ala Val Asp Pro Lys Val Ile Ser Ile Ala Asn Arg Val Ala Glu Ile
145                 150                 155                 160

Val Tyr Ser Trp Pro Pro Gln Ala Thr Gln Ala Gly Gly Phe Lys
                165                 170                 175

Ser Lys Glu Ile Phe Val Thr Glu Gly Leu Ser Phe Gln Leu Gln Gly
            180                 185                 190

His Val Pro Val Ala Ser Ser Lys Lys Asp Glu Glu Gln Ile
        195                 200                 205

Leu Ala Lys Ile Val Glu Leu Leu Lys Tyr Ser Gly Asp Gln Leu Glu
    210                 215                 220

Arg Lys Leu Lys Lys Asp Lys Ala Leu Met Gly His Phe Gln Asp Gly
225                 230                 235                 240
```

```
Leu Ser Tyr Ser Val Phe Lys Thr Ile Thr Asp Gln Val Leu Met Gly
                245                 250                 255

Val Asp Pro Arg Gly Glu Ser Glu Val Lys Ala Gln Gly Phe Lys Ala
            260                 265                 270

Ala Leu Val Ile Asp Val Thr Ala Lys Leu Thr Ala Ile Asp Asn His
        275                 280                 285

Pro Met Asn Arg Val Leu Gly Phe Gly Thr Lys Tyr Leu Lys Glu Asn
    290                 295                 300

Phe Ser Pro Trp Ile Gln Gln His Gly Gly Trp Lys Ile Leu Gly
305                 310                 315                 320

Ile Ser His Glu Glu Val Asp
                325

<210> SEQ ID NO 3
<211> LENGTH: 954
<212> TYPE: DNA
<213> ORGANISM: Homo sapiens
<220> FEATURE:
<221> NAME/KEY: CDS
<222> LOCATION: (196)..(954)

<400> SEQUENCE: 3
aatgacatga cagccattcc gtggccaggg acaccactgc ccaagctgga gaccacgagg      60
attcagggac tgaagccagc atgggaattc ctggtttgag atcagagtcc tgagtacctc     120
gtgggaactt gggcactcat ccgcaggagg tctagacccc agagaattcc cttgagtcta     180
aggcacaggc ccaac atg tgt agc acc agt ggg tgt gac ctg gaa gaa atc     231
                  Met Cys Ser Thr Ser Gly Cys Asp Leu Glu Glu Ile
                    1               5                  10 ccc cta gat gat gat gac cta aac acc ata gaa ttc aaa atc ctc gcc     279
Pro Leu Asp Asp Asp Asp Leu Asn Thr Ile Glu Phe Lys Ile Leu Ala
            15                  20                  25 tac tac acc aga cat cat gtc ttc aag agc acc cct gct ctc ttc tca     327
Tyr Tyr Thr Arg His His Val Phe Lys Ser Thr Pro Ala Leu Phe Ser
        30                  35                  40 cca aag ctg ctg aga aca aga agt ttg tcc cag agg ggc ctg ggg aat     375
Pro Lys Leu Leu Arg Thr Arg Ser Leu Ser Gln Arg Gly Leu Gly Asn
 45                  50                  55                  60 tgt tca gca aat gag tca tgg aca gag gtg tca tgg cct tgc aga aat     423
Cys Ser Ala Asn Glu Ser Trp Thr Glu Val Ser Trp Pro Cys Arg Asn
                 65                  70                  75 tcc caa tcc agt gag aag gcc ata aac ctt ggc aag aaa aag tct tct     471
Ser Gln Ser Ser Glu Lys Ala Ile Asn Leu Gly Lys Lys Lys Ser Ser
             80                  85                  90 tgg aaa gca ttc ttt gga gta gtg gag aag gaa gat tcg cag agc acg     519
Trp Lys Ala Phe Phe Gly Val Val Glu Lys Glu Asp Ser Gln Ser Thr
         95                 100                 105 cct gcc aag gtc tct gct cag ggt caa agg acg ttg gaa tac caa gat     567
Pro Ala Lys Val Ser Ala Gln Gly Gln Arg Thr Leu Glu Tyr Gln Asp
    110                 115                 120 tcg cac agc cag cag tgg tcc agg tgt ctt tct aac gtg gag cag tgc     615
Ser His Ser Gln Gln Trp Ser Arg Cys Leu Ser Asn Val Glu Gln Cys
125                 130                 135                 140 ttg gag cat gaa gct gtg gac ccc aaa gtc att tcc att gcc aac cga     663
Leu Glu His Glu Ala Val Asp Pro Lys Val Ile Ser Ile Ala Asn Arg
                145                 150                 155 gta gct gaa att gtt tac tcc tgg cca cca caa gcg acc cag gca         711
Val Ala Glu Ile Val Tyr Ser Trp Pro Pro Gln Ala Thr Gln Ala
            160                 165                 170
```

-continued

```
gga ggc ttc aag tcc aaa gag att ttt gta act gag ggt ctc tcc ttc    759
Gly Gly Phe Lys Ser Lys Glu Ile Phe Val Thr Glu Gly Leu Ser Phe
        175                 180                 185 cag ctc caa ggc cac gtg cct gta gct tca agt tct aag aaa gat gaa    807
Gln Leu Gln Gly His Val Pro Val Ala Ser Ser Ser Lys Lys Asp Glu
    190                 195                 200 gaa gaa caa ata cta gcc aaa att gtt gag ctg ctg aaa tat tca gga    855
Glu Glu Gln Ile Leu Ala Lys Ile Val Glu Leu Leu Lys Tyr Ser Gly
205                 210                 215                 220 gat cag ttg gaa aga aag gac act gcc ttc atc ccc att ccc ttg gtt    903
Asp Gln Leu Glu Arg Lys Asp Thr Ala Phe Ile Pro Ile Pro Leu Val
                225                 230                 235 gac acc agc atc cag ggt ttt cca cag gat ggt ttg atg gcc tgc att    951
Asp Thr Ser Ile Gln Gly Phe Pro Gln Asp Gly Leu Met Ala Cys Ile
            240                 245                 250 tga                                                                954
```

<210> SEQ ID NO 4
<211> LENGTH: 252
<212> TYPE: PRT
<213> ORGANISM: Homo sapiens

<400> SEQUENCE: 4

Met Cys Ser Thr Ser Gly Cys Asp Leu Glu Glu Ile Pro Leu Asp Asp
1               5                   10                  15

Asp Asp Leu Asn Thr Ile Glu Phe Lys Ile Leu Ala Tyr Tyr Thr Arg
            20                  25                  30

His His Val Phe Lys Ser Thr Pro Ala Leu Phe Ser Pro Lys Leu Leu
        35                  40                  45

Arg Thr Arg Ser Leu Ser Gln Arg Gly Leu Gly Asn Cys Ser Ala Asn
    50                  55                  60

Glu Ser Trp Thr Glu Val Ser Trp Pro Cys Arg Asn Ser Gln Ser Ser
65                  70                  75                  80

Glu Lys Ala Ile Asn Leu Gly Lys Lys Ser Ser Trp Lys Ala Phe
                85                  90                  95

Phe Gly Val Val Glu Lys Glu Asp Ser Gln Ser Thr Pro Ala Lys Val
            100                 105                 110

Ser Ala Gln Gly Gln Arg Thr Leu Glu Tyr Gln Asp Ser His Ser Gln
        115                 120                 125

Gln Trp Ser Arg Cys Leu Ser Asn Val Glu Gln Cys Leu Glu His Glu
    130                 135                 140

Ala Val Asp Pro Lys Val Ile Ser Ile Ala Asn Arg Val Ala Glu Ile
145                 150                 155                 160

Val Tyr Ser Trp Pro Pro Gln Ala Thr Gln Ala Gly Gly Phe Lys
                165                 170                 175

Ser Lys Glu Ile Phe Val Thr Glu Gly Leu Ser Phe Gln Leu Gln Gly
            180                 185                 190

His Val Pro Val Ala Ser Ser Ser Lys Lys Asp Glu Glu Glu Gln Ile
        195                 200                 205

Leu Ala Lys Ile Val Glu Leu Leu Lys Tyr Ser Gly Asp Gln Leu Glu
    210                 215                 220

Arg Lys Asp Thr Ala Phe Ile Pro Ile Pro Leu Val Asp Thr Ser Ile
225                 230                 235                 240

Gln Gly Phe Pro Gln Asp Gly Leu Met Ala Cys Ile
                245                 250

```
<210> SEQ ID NO 5
<211> LENGTH: 9
<212> TYPE: PRT
<213> ORGANISM: Homo sapiens

<400> SEQUENCE: 5

Leu Lys Tyr Ser Gly Asp Gln Leu Glu
  1               5

<210> SEQ ID NO 6
<211> LENGTH: 10
<212> TYPE: PRT
<213> ORGANISM: Homo sapiens

<400> SEQUENCE: 6

Pro Trp Ile Gln Gln His Gly Gly Trp Glu
  1               5                  10

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 7
gtacttggtg ccaaagccca gg                                       22

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 8
gacatgatgt ctggtgtagt aggcgagg                                 28

<210> SEQ ID NO 9
<211> LENGTH: 15
<212> TYPE: PRT
<213> ORGANISM: Homo sapiens

<400> SEQUENCE: 9

Ile Val Glu Leu Leu Lys Tyr Ser Gly Asp Gln Leu Glu Arg Lys
  1               5                  10                  15

<210> SEQ ID NO 10
<211> LENGTH: 15
<212> TYPE: PRT
<213> ORGANISM: Homo sapiens

<400> SEQUENCE: 10

Leu Ser Glu Cys Leu Lys Arg Ile Gly Asp Glu Leu Asp Ser Asn
  1               5                  10                  15

<210> SEQ ID NO 11
<211> LENGTH: 15
<212> TYPE: PRT
<213> ORGANISM: Homo sapiens

<400> SEQUENCE: 11

Val Gly Arg Gln Leu Ala Ile Ile Gly Asp Asp Ile Asn Arg Arg
  1               5                  10                  15
```

```
<210> SEQ ID NO 12
<211> LENGTH: 15
<212> TYPE: PRT
<213> ORGANISM: Homo sapiens

<400> SEQUENCE: 12

Ile Ala Arg His Leu Ala Gln Val Gly Asp Ser Met Asp Arg Ser
 1               5                  10                  15

<210> SEQ ID NO 13
<211> LENGTH: 15
<212> TYPE: PRT
<213> ORGANISM: Homo sapiens

<400> SEQUENCE: 13

Leu Ala Leu Arg Leu Ala Cys Ile Gly Asp Glu Met Asp Val Ser
 1               5                  10                  15

<210> SEQ ID NO 14
<211> LENGTH: 15
<212> TYPE: PRT
<213> ORGANISM: Homo sapiens

<400> SEQUENCE: 14

Ala Leu Glu Thr Leu Arg Arg Val Gly Asp Gly Val Gln Arg Asn
 1               5                  10                  15

<210> SEQ ID NO 15
<211> LENGTH: 15
<212> TYPE: PRT
<213> ORGANISM: Homo sapiens

<400> SEQUENCE: 15

Val Lys Gln Ala Leu Arg Glu Ala Gly Asp Glu Phe Glu Leu Arg
 1               5                  10                  15

<210> SEQ ID NO 16
<211> LENGTH: 15
<212> TYPE: PRT
<213> ORGANISM: Homo sapiens

<400> SEQUENCE: 16

Leu His Gln Ala Met Arg Ala Ala Gly Asp Glu Phe Glu Thr Arg
 1               5                  10                  15

<210> SEQ ID NO 17
<211> LENGTH: 15
<212> TYPE: PRT
<213> ORGANISM: Homo sapiens

<400> SEQUENCE: 17

Val His Leu Thr Leu Arg Gln Ala Gly Asp Asp Phe Ser Arg Arg
 1               5                  10                  15

<210> SEQ ID NO 18
<211> LENGTH: 8
<212> TYPE: PRT
<213> ORGANISM: Homo sapiens

<400> SEQUENCE: 18

Trp Ile Gln Gln His Gly Gly Trp
 1               5

<210> SEQ ID NO 19
<211> LENGTH: 8
```

```
<212> TYPE: PRT
<213> ORGANISM: Homo sapiens

<400> SEQUENCE: 19

Trp Ile Gln Asp Gln Gly Gly Trp
 1               5

<210> SEQ ID NO 20
<211> LENGTH: 8
<212> TYPE: PRT
<213> ORGANISM: Homo sapiens

<400> SEQUENCE: 20

Trp Ile Ala Gln Arg Gly Gly Trp
 1               5

<210> SEQ ID NO 21
<211> LENGTH: 8
<212> TYPE: PRT
<213> ORGANISM: Homo sapiens

<400> SEQUENCE: 21

Trp Leu Arg Arg Arg Gly Gly Trp
 1               5

<210> SEQ ID NO 22
<211> LENGTH: 8
<212> TYPE: PRT
<213> ORGANISM: Homo sapiens

<400> SEQUENCE: 22

Trp Ile Arg Gln Asn Gly Gly Trp
 1               5

<210> SEQ ID NO 23
<211> LENGTH: 8
<212> TYPE: PRT
<213> ORGANISM: Homo sapiens

<400> SEQUENCE: 23

Trp Leu Val Lys Gln Arg Gly Trp
 1               5

<210> SEQ ID NO 24
<211> LENGTH: 8
<212> TYPE: PRT
<213> ORGANISM: Homo sapiens

<400> SEQUENCE: 24

Trp Ile Gln Glu Asn Gly Gly Trp
 1               5

<210> SEQ ID NO 25
<211> LENGTH: 8
<212> TYPE: PRT
<213> ORGANISM: Homo sapiens

<400> SEQUENCE: 25

Trp Ile His Ser Ser Gly Gly Trp
 1               5

<210> SEQ ID NO 26
<211> LENGTH: 8
<212> TYPE: PRT
<213> ORGANISM: Homo sapiens
```

```
<400> SEQUENCE: 26

Trp Ile Gln Asp Asn Gly Gly Trp
  1               5

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: synthetic
      primer

<400> SEQUENCE: 27
ggctcgagcg atgtgtagca ccagtgggtg tgacc                            35

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: synthetic
      primer

<400> SEQUENCE: 28
ccaagcttta agtctacttc ttcatgtgat atccc                            35

<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence: synthetic
      primer

<400> SEQUENCE: 29
ccaagcttta aaatgcaggc catcaaacc                                   29

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: synthetic
      primer

<400> SEQUENCE: 30
ggctcgagcg atgtgtagca ccagtgggtg tgacc                            35

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: synthetic
      primer

<400> SEQUENCE: 31
ccggatccgg ctagtatttg ttcttcttca tcttt                            35

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: synthetic
      primer
```

```
<400> SEQUENCE: 32
ccggatccga cactgccttc atccccattc cc                                   32

<210> SEQ ID NO 33
<211> LENGTH: 29
<212> TYPE: DNA
<213> ORGANISM: Artificial Sequence
<220> FEATURE:
<223> OTHER INFORMATION: Description of Artificial Sequence:synthetic
      primer

<400> SEQUENCE: 33
ccaagcttta aaatgcaggc catcaaacc                                       29

<210> SEQ ID NO 34
<211> LENGTH: 43
<212> TYPE: DNA
<213> ORGANISM: Artificial Sequence
<220> FEATURE:
<223> OTHER INFORMATION: Description of Artificial Sequence: synthetic
      primer

<400> SEQUENCE: 34
gccaaaattg ttgagctgga gaatattca ggagatcagt tgg                        43

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: synthetic
      primer

<400> SEQUENCE: 35
ccaactgatc tcctgaatat ttctccagct caacaatttt ggc                       43

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: synthetic
      primer

<400> SEQUENCE: 36
ctgagggtct ctccttccag ctccaagg                                        28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: synthetic
      primer

<400> SEQUENCE: 37
ggccgtgacg tctattacaa gggcagcc                                        28

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: synthetic
      primer
```

-continued

```
<400> SEQUENCE: 38
caagggaatg gggatgaagg cagtgtc                                         27

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: synthetic
      primer

<400> SEQUENCE: 39
tgaaggtcgg agtcaacgga tttggt                                          26

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: synthetic
      primer

<400> SEQUENCE: 40
catgtgggcc atgaggtcca ccac                                            24

<210> SEQ ID NO 41
<211> LENGTH: 987
<212> TYPE: DNA
<213> ORGANISM: Mus musculus
<220> FEATURE:
<221> NAME/KEY: CDS
<222> LOCATION: (1)..(987)
<221> NAME/KEY: unsure
<222> LOCATION: (319)
<223> OTHER INFORMATION: n=unknown nucleotide

<400> SEQUENCE: 41 atg tgc agc acc agt gtg tat gac ctg gaa gac att ccc ctg gag gat       48
Met Cys Ser Thr Ser Val Tyr Asp Leu Glu Asp Ile Pro Leu Glu Asp
 1               5                  10                  15 gat gat cca aac agc ata gag ttc aaa atc ctg gcc ttc tac gcc aga       96
Asp Asp Pro Asn Ser Ile Glu Phe Lys Ile Leu Ala Phe Tyr Ala Arg
             20                  25                  30 cac cat gtc ttc aag aac acc ccg gct gtc ttc tcg ccc aag ctc tcc      144
His His Val Phe Lys Asn Thr Pro Ala Val Phe Ser Pro Lys Leu Ser
         35                  40                  45 aga aca agg agt ctg tcc cag aaa gcc ctg ggg act tgg tca act gat      192
Arg Thr Arg Ser Leu Ser Gln Lys Ala Leu Gly Thr Trp Ser Thr Asp
     50                  55                  60 tcc tgg aca cag gta tca ttg cct tgc aga ggt tcc ccc tcc agc gaa      240
Ser Trp Thr Gln Val Ser Leu Pro Cys Arg Gly Ser Pro Ser Ser Glu
 65                  70                  75                  80 aag aac atc agc ttg ggc aag aag aag tct tct tgg aga aca ctc ttc      288
Lys Asn Ile Ser Leu Gly Lys Lys Lys Ser Ser Trp Arg Thr Leu Phe
                 85                  90                  95 agg gtg gcc gag aag gag gaa ggc ctg ccg ngc tcc cca aag gag atc      336
Arg Val Ala Glu Lys Glu Glu Gly Leu Pro Xaa Ser Pro Lys Glu Ile
            100                 105                 110 cga gct cag ggt cct cag ggc ccc ttc ccg gta gag cgg cag agt ggc      384
Arg Ala Gln Gly Pro Gln Gly Pro Phe Pro Val Glu Arg Gln Ser Gly
        115                 120                 125 ttc cac aac cag cac tgg ccc agg tct ctg agc agt gtg gag cag ccc      432
Phe His Asn Gln His Trp Pro Arg Ser Leu Ser Ser Val Glu Gln Pro
    130                 135                 140
```

```
tgg aga gtg aag ttg tgg att cca aag tgg ctt gta ttg cca aca gag      480
Trp Arg Val Lys Leu Trp Ile Pro Lys Trp Leu Val Leu Pro Thr Glu
145                 150                 155                 160 tgg ctg aaa ttg ttt act cct ggc cac cac cag atg tca tcc aca gcc      528
Trp Leu Lys Leu Phe Thr Pro Gly His His Gln Met Ser Ser Thr Ala
                165                 170                 175 agg gag gaa gcc agc tca aag aga ggg tct cgg aga ttt ttg tac ttc      576
Arg Glu Glu Ala Ser Ser Lys Arg Gly Ser Arg Arg Phe Leu Tyr Phe
            180                 185                 190 agg ttt gaa gga cct tgg gac tct aag aat aaa gat ggt gaa gac caa      624
Arg Phe Glu Gly Pro Trp Asp Ser Lys Asn Lys Asp Gly Glu Asp Gln
        195                 200                 205 ata ata agc aag att gtt gag ctg ctg aaa tcc tcg ggg gat cag ttg      672
Ile Ile Ser Lys Ile Val Glu Leu Leu Lys Ser Ser Gly Asp Gln Leu
    210                 215                 220 gga aga gag ata aag aaa gac aag gct ttg atg agc agc ttc cag gac      720
Gly Arg Glu Ile Lys Lys Asp Lys Ala Leu Met Ser Ser Phe Gln Asp
225                 230                 235                 240 ggg ctg tcc tac tca acg ttc aag acc atc aca gac ctg ttc ctg agg      768
Gly Leu Ser Tyr Ser Thr Phe Lys Thr Ile Thr Asp Leu Phe Leu Arg
                245                 250                 255 gac gtg gac acc aga gga gaa tca gag gtc aaa gct cgg ggc ttc aag      816
Asp Val Asp Thr Arg Gly Glu Ser Glu Val Lys Ala Arg Gly Phe Lys
            260                 265                 270 gct gcc ctt gca ata gac gcc atc gcc aag ctc acg gca tcg gac aac      864
Ala Ala Leu Ala Ile Asp Ala Ile Ala Lys Leu Thr Ala Ser Asp Asn
        275                 280                 285 cac cca atg aat aga atg ctg ggc ttc ggg acc aag tac cta aaa gag      912
His Pro Met Asn Arg Met Leu Gly Phe Gly Thr Lys Tyr Leu Lys Glu
    290                 295                 300 tac ttc tcc ccc tgg gtt cag cag aat ggc gga tgg gaa aaa ata ctt      960
Tyr Phe Ser Pro Trp Val Gln Gln Asn Gly Gly Trp Glu Lys Ile Leu
305                 310                 315                 320 ggg atc tca cat gaa gaa gta gac tga                                  987
Gly Ile Ser His Glu Glu Val Asp
                325

<210> SEQ ID NO 42
<211> LENGTH: 328
<212> TYPE: PRT
<213> ORGANISM: Mus musculus
<220> FEATURE:
<221> NAME/KEY: 107
<222> LOCATION: unsure
<223> OTHER INFORMATION: Xaa = unknown amino acid

<400> SEQUENCE: 42

Met Cys Ser Thr Ser Val Tyr Asp Leu Glu Asp Ile Pro Leu Glu Asp
  1               5                  10                  15

Asp Asp Pro Asn Ser Ile Glu Phe Lys Ile Leu Ala Phe Tyr Ala Arg
                 20                  25                  30

His His Val Phe Lys Asn Thr Pro Ala Val Phe Ser Pro Lys Leu Ser
             35                  40                  45

Arg Thr Arg Ser Leu Ser Gln Lys Ala Leu Gly Thr Trp Ser Thr Asp
         50                  55                  60

Ser Trp Thr Gln Val Ser Leu Pro Cys Arg Gly Ser Pro Ser Ser Glu
 65                  70                  75                  80

Lys Asn Ile Ser Leu Gly Lys Lys Ser Ser Trp Arg Thr Leu Phe
                 85                  90                  95
```

```
Arg Val Ala Glu Lys Glu Gly Leu Pro Xaa Ser Pro Lys Glu Ile
            100                 105                 110

Arg Ala Gln Gly Pro Gln Gly Pro Phe Pro Val Glu Arg Gln Ser Gly
        115                 120                 125

Phe His Asn Gln His Trp Pro Arg Ser Leu Ser Ser Val Glu Gln Pro
    130                 135                 140

Trp Arg Val Lys Leu Trp Ile Pro Lys Trp Leu Val Leu Pro Thr Glu
145                 150                 155                 160

Trp Leu Lys Leu Phe Thr Pro Gly His His Gln Met Ser Ser Thr Ala
                165                 170                 175

Arg Glu Glu Ala Ser Ser Lys Arg Gly Ser Arg Arg Phe Leu Tyr Phe
            180                 185                 190

Arg Phe Glu Gly Pro Trp Asp Ser Lys Asn Lys Asp Gly Glu Asp Gln
        195                 200                 205

Ile Ile Ser Lys Ile Val Glu Leu Leu Lys Ser Ser Gly Asp Gln Leu
    210                 215                 220

Gly Arg Glu Ile Lys Lys Asp Lys Ala Leu Met Ser Ser Phe Gln Asp
225                 230                 235                 240

Gly Leu Ser Tyr Ser Thr Phe Lys Thr Ile Thr Asp Leu Phe Leu Arg
                245                 250                 255

Asp Val Asp Thr Arg Gly Glu Ser Glu Val Lys Ala Arg Gly Phe Lys
            260                 265                 270

Ala Ala Leu Ala Ile Asp Ala Ile Ala Lys Leu Thr Ala Ser Asp Asn
        275                 280                 285

His Pro Met Asn Arg Met Leu Gly Phe Gly Thr Lys Tyr Leu Lys Glu
    290                 295                 300

Tyr Phe Ser Pro Trp Val Gln Gln Asn Gly Gly Trp Glu Lys Ile Leu
305                 310                 315                 320

Gly Ile Ser His Glu Glu Val Asp
                325

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: synthetic
      primer

<400> SEQUENCE: 43
gggctcgaga tgtgcagcac cagtgtgtat g                              31

<210> SEQ ID NO 44
<211> LENGTH: 35
<212> TYPE: DNA
<213> ORGANISM: Artificial Sequence
<220> FEATURE:
<223> OTHER INFORMATION: Description of Artificial Sequence: synthetic
      primer

<400> SEQUENCE: 44
ccaagcttta agtctacttc ttcatgtgat atccc                          35
```

BCL-G POLYPEPTIDES, ENCODING NUCLEIC ACIDS AND METHODS OF USE

This application claims the benefit of U.S. Provisional Application No. 60/287,581, filed Dec. 14, 1999, which was converted from U.S. Ser. No. 09/461,641, filed Dec. 14, 1999, which is incorporated herein by reference.

This invention was made with government support under grant number GM60554 awarded by the National Institutes of Health. The government has certain rights in the invention.

BACKGROUND OF THE INVENTION

The present invention relates generally to regulation of programmed cell death and more specifically to molecules that promote programmed cell death.

In essentially all self-renewing tissues, a balance is struck between cell production by mitogenesis and cell loss due to programmed cell death, thereby maintaining total cell numbers within a physiologically appropriate range. In pathological conditions, however, the balance in cell production and cell loss can be disrupted. In cancer, for example, an increased amount of cell production due to a shortened cell cycle time or a decreased amount of cell death due to dysregulation of a programmed cell death pathway results in the growth of a tumor.

With regard to programmed cell death, a variety of stimuli, which occur either external or internal to the cell, initiate a pathway that ultimately results in apoptosis of the cell. As is common for most signal transduction pathways, the various different stimuli that induce apoptosis likely initiate the process of programmed cell death through specific pathways. However, most if not all of these initial pathways converge at a common point that generally involves a member of the Bcl-2 family of proteins.

The Bcl-2 family of proteins regulate a distal step in the evolutionarily conserved pathway for programmed cell death and apoptosis, with some members of this family functioning as suppressors of cell death (anti-apoptotic proteins) and other members functioning as promoters of cell death (pro-apoptotic proteins). Overexpression of the anti-apoptotic protein, Bcl-2, for example, blocks neuronal cell death that otherwise is induced in vitro by various stimuli, including neurotrophic factor withdrawal, various oxidants, glucose deprivation, certain neurotrophic viruses, and amyloid β-peptide. In addition, Bcl-2 is overexpressed in some tumor cells and, in part, may contribute to tumor growth by altering the balance between cell division and cell death.

The Bcl-2 family of proteins are critical regulators of pathways involved in apoptosis, acting to either inhibit or promote cell death (Reed, *Nature* 387:773-776 (1997); Green and Reed, *Science* 281:1309-1312 (1998); Reed, *Oncogene* 17:3225-3236 (1998); Reed, *Curr. Opin. Oncol.* 11:68-75 (1999)). The Bcl-2 family members can be divided into two groups, those with anti-apoptotic activity, including Bcl-2 and Bcl-$X_L$, and those with pro-apoptotic activity, including Bax and Bak.

Four distinct domains have been identified in Bcl-2 family members, designated BH1 to BH4. The BH4 domain is a domain that mediates interactions with a variety of cellular proteins (Reed, supra, 1998). The BH1, BH2 and BH3 domains form a binding pocket for dimerization with other Bcl-2 members having a BH3 domain, which also functions as a ligand that binds to the dimerization binding pocket. The dimerization function of the Bcl-2 members is an important mechanism for regulating apoptosis in that heterodimerization of pro-apoptotic Bcl-2 members with anti-apoptotic Bcl-2 members can regulate the cellular apoptotic pathways. Some Bcl-2 members only have a BH3 domain and therefore function as trans-dominant inhibitors of anti-apopototic proteins such as Bcl-2 and Bcl-$X_L$ (Reed, supra, 1998).

Another function of Bcl-2 members is the formation of ion channels. Bcl-2 members can localize to the mitochondrial membrane, and the formation of ion pores that alter the permeability of mitochondria is thought to be an important signaling mechanism for the induction of apoptosis. Thus, Bcl-2 members use at least three mechanisms to regulate apoptotic activity: dimerization with Bcl-2 members, formation of ion pores in mitochondria, and binding to non-Bcl-2 members that function as signaling molecules.

In comparison, overexpression of the pro-apoptotic protein, Bax, for example, promotes cell death when triggered by a variety of inducers of apoptosis, including growth factor withdrawal, ionizing radiation, and anti-Fas antibody. In addition, elevations in Bax expression occur in association with cell death induced by a variety of stimuli, including neuronal cell death that occurs due to ischemia, epilepsy, spinal cord injury, and certain neurodegenerative diseases such as Parkinson's disease and Alzheimer's disease.

Although aberrant expression of members of the Bcl-2 family of proteins is associated with various pathologic conditions, the mechanisms by which these proteins mediate their action is not known. Often, the action of a protein can be inferred from its structural relationship to other proteins, whose functions are known. However, while the Bcl-2 family proteins share certain structural homologies with each other, they do not share substantial amino acid sequence homology with other proteins, further hindering attempts to understand how the Bcl-2 family proteins such as Bcl-2 and Bax regulate cell death.

Thus, a need exists to identify proteins involved in the programmed cell death pathway and to identify methods of regulating programmed cell death for therapeutic applications, including treatment of cancer. The present invention satisfies this need and provides related advantages as well.

SUMMARY OF THE INVENTION

In accordance with the present invention, there are provided Bcl-G polypeptides and encoding nucleic acid molecules. The invention polypeptides and encoding nucleic acids are useful for modulating apoptosis by altering the expression or activity of Bcl-G. The Bcl-G polypeptides and encoding nucleic acids can be advantageously used to diagnose or treat cancer, in particular prostate, ovarian and leukemia. Furthermore, the Bcl-G polypeptides and encoding nucleic acids are useful to generate or screen for agents that can alter Bcl-G activity or expression, which can further be used to treat cancer. Bcl-G polypeptides include Bcl-$G_L$ and Bcl-$G_S$.

The invention also provides vectors containing Bcl-G nucleic acids, host cells containing such vectors, Bcl-G antisense nucleic acids and related compositions. The invention additionally provides Bcl-G oligonucleotides that can be used to hybridize to or amplify a Bcl-G nucleic acid. Anti-Bcl-G specific antibodies are also provided. Further provided are kits containing Bcl-G nucleic acids or Bcl-G specific antibodies. Such kits and reagents can be used to diagnose cancer, monitor response to therapy, or predict the prognosis of a cancer patient. The invention additionally provides methods of modulating apoptosis using Bcl-G polypeptides, encoding nucleic acids, or compounds that modulate the activity or expression of Bcl-G polypeptides. The methods for modulating apoptosis can be used to treat diseases such as cancer.

BRIEF DESCRIPTION OF THE DRAWINGS

FIG. 1 shows the nucleotide sequence of human Bcl-G$_L$ CDNA (SEQ ID NO:1).

FIG. 2 shows the nucleotide sequence of the coding region of human Bcl-G$_L$ cDNA (nucleotide 196-1179 of SEQ ID NO:1) and the encoded amino acid sequence (SEQ ID NO:2). Bcl-G$_L$ contains a BH3 domain ($^{216}$LKYSGDQLE$^{224}$; SEQ ID NO:5) and a BH2 domain ($^{307}$PWIQQHGGWE$^{316}$; SEQ ID NO:6).

FIG. 3 shows the nucleotide sequence of human Bcl-G$_S$ cDNA (SEQ ID NO:3)

FIG. 4 shows the nucleotide sequence of the coding region of human Bcl-G$_S$ cDNA (nucleotide 196-954 of SEQ ID NO:3) and the encoded amino acid sequence (SEQ ID NO:4). Bcl-G$_S$ contains only the BH3 domain ($^{216}$LKYSGDQLE$^{224}$; SEQ ID NO:5).

FIG. 5A shows the predicted amino acid sequences of the Bcl-G$_L$ and Bcl-G$_S$ proteins, with the BH2 and BH3 domains in bold-type and residue numbers indicated. The predicted proteins are identical from residues 1-226. The unique C-terminal region of Bcl-G$_S$ is indicated in italics type. FIG. 5B shows an alignment of the BH2 domains of Bcl-G$_L$ (SEQ ID NO:9) and several other Bcl-2 family proteins (SEQ ID NOS:10-17, respectively). Identical and similar residues are shown in black and gray blocks, respectively. FIG. 5C shows an alignment of the BH3 domains Bcl-G (SEQ ID NO:18) and several other Bcl-2 family proteins (SEQ ID NOS:19-26, respectively). FIG. 5D shows the exon-intron organization of the BCL-G gene. The BCL-G gene contains 6 exons, spanning a ~30 kb region of chromosome 12. Alternative splicing at the 5'-end of exon 5 accounts for the production of the Bcl-G$_L$ and Bcl-G$_S$ proteins, where splice-acceptor sites at nucleotide positions 63,870 versus 63,797 in BAC clone RPCI 11-267J23 (GenBank AC007537) are utilized for Bcl-G$_L$ and Bcl-G$_S$, respectively. The positions of the start and termination codons are indicated, with coding regions in gray blocks and non-coding 5'-UTR and 3'-UTR sequence in open blocks. The BH3 domain is located in exon 4 of both Bcl-G$_L$ and Bcl-G$_S$, while the BH2 domain resides in exon 5 of Bcl-G$_L$.

FIG. 9A shows the results of transfecting plasmids encoding GFP, GFP-Bcl-G$_S$, or GFP-Bcl-G$_L$ into Cos-7 cells alone or in combination with a plasmid encoding Bcl-X$_L$. Apoptosis was examined by DAPI staining at 24 h post-transfection (mean+ SD; n=3) (top). Levels of GFP and GFP-Bcl-G fusion proteins were examined by immunoblotting lysates from transfected Cos-7 cells (20 μg per lane) and anti-GFP antibody with ECL-based detection (middle). Equal loading was confirmed by reprobing the same membrane with anti-Tubulin antibody (bottom). FIG. 9B shows the results of transfecting plasmids encoding GFP, GFP-Bcl-G$_S$ or the mutant proteins, Bcl-G$_S$ (ΔBH3) and GFP-Bcl-G$_S$ (L216E) into Cos-7 cells. The percentage of apoptotic cells was examined 1 day later as above (top). Protein expression was assessed by immunoblotting as above, using anti-GFP (middle) or anti-Tubulin (bottom) antibodies.

FIG. 11 shows microscopic evaluation of intracellular distributions of Bcl-G$_L$ and Bcl-Gs. Plasmids encoding GFP (A), GFP-Bcl-G$_L$ (B), GFP-Bcl-G$_S$ (C), and GFP-Bcl-G$_S$ (ΔBH3) (D) were transfected into Cos-7 cells. Cells were fixed 1 day later and examined by confocal microscopy.

DETAILED DESCRIPTION OF THE INVENTION

Figure 5:
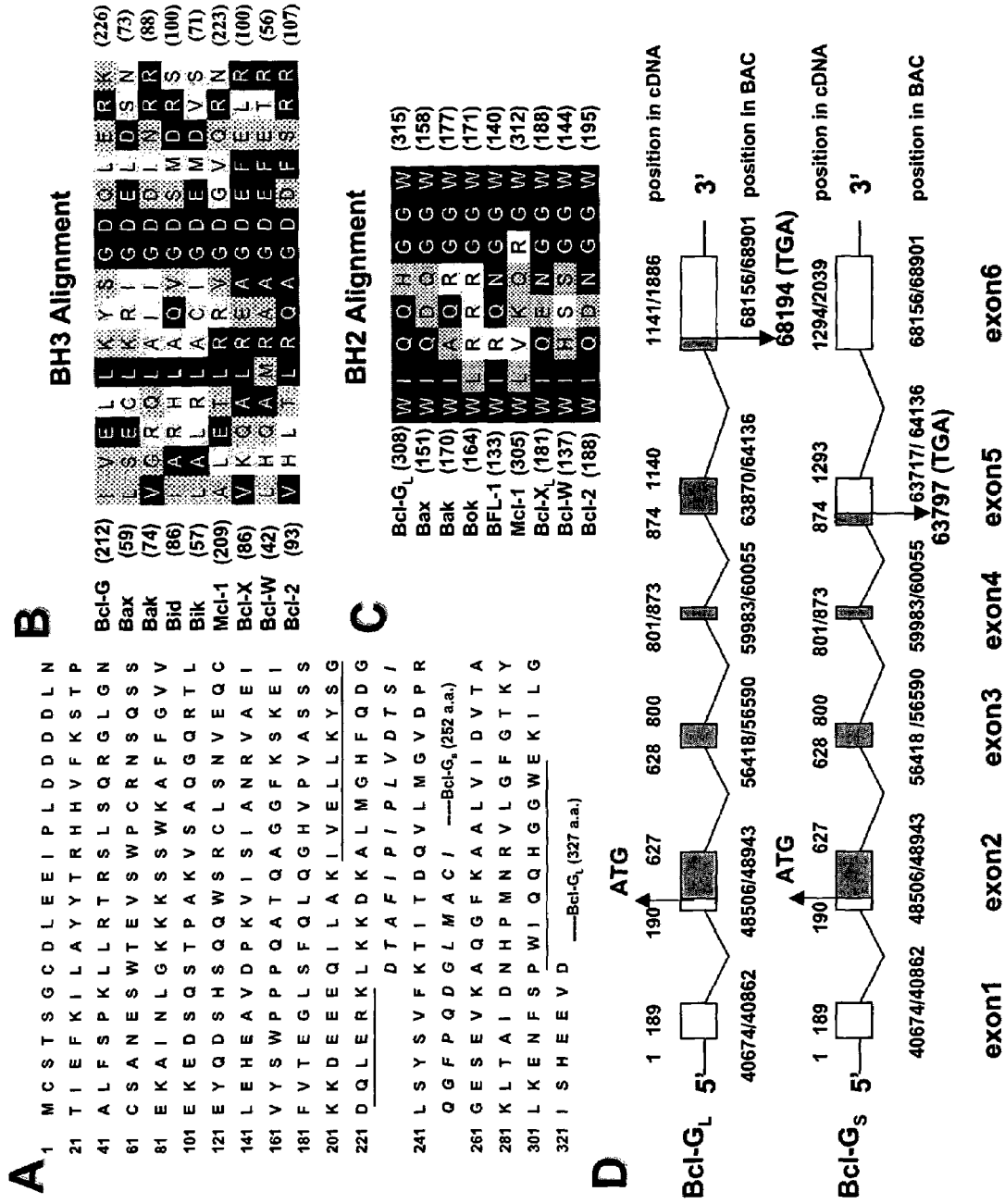
FIG. 5 shows sequence analysis of Bcl-G cDNAs.

In accordance with the present invention, there are provided nucleic acids encoding Bcl-G polypeptides, or functional polypeptide fragments thereof. As used herein, the term "Bcl-G" refers to sub-family members of the Bcl-2 family of proteins, wherein said Bcl-G comprises a BH3 domain (SEQ ID NOS:5 or 9). The human Bcl-G gene has been found to map to chromosome 12p12.3 (Example II). This region of chromosome 12 is frequently deleted in cancer cells, in particular in acute lymphoblastic leukemia (ALL) and other solid tumor cells (Baens et al., (1999) *Genomics* 56:40-50 (1999); Hatta et al., *Br. J. Cancer* 75:1256-1262 (1997); Kibel et al., *Cancer Res.* 58:5652-5655 (1998); Baccichet et al., *Br. J. Haematol.* 99:107-114 (1997); Aissani et al., *Leuk. Lymphoma* 34:231-239). This region is deleted in a subset of prostate (approximately 50%), ovarian (approximately 30%) and leukemias (approximately 30%). Therefore, Bcl-G can function as a tumor suppressor. Furthermore, the presence or absence of Bcl-G nucleic acid or polypeptide or changes in Bcl-G nucleic acid or polypeptide expression, can serve as a marker for predisposition or progression of cancer, for example, prostate, ovarian and leukemia. Thus, the invention Bcl-G nucleic acids and/or polypeptides can be used for screening for cancer and/or for developing drug candidates for the treatment of cancer. Invention Bcl-G nucleic acids and/or polypeptides can also be used for discovery of drugs, as disclosed herein, that suppress autoimmunity, inflammation, allergy, allograph rejection, sepsis, and other diseases, including inflammatory diseases.

A new member of the Bcl-2 family was identified, Bcl-G (see Examples). The human BCL-G gene consists of 6 exons, resides on chromosome 12p12, and encodes two proteins through alternative mRNA splicing: Bcl-G (long) and Bcl-G (short) consisting of 327 and 252 (length) amino acids, respectively. Bcl-G$_L$ and Bcl-G$_S$ are identical in their first 226 amino-acids but diverge thereafter. Among the Bcl-2 Homology (BH) domains previously recognized in Bcl-2 family proteins, the BH3 domain is found in both Bcl-G$_L$ and Bcl-G$_s$, but only the longer Bcl-G$_L$ protein possesses a BH2 domain. Bcl-G$_L$ mRNA is expressed widely in normal human tissues, whereas Bcl-G$_L$ mRNA was found only in testis. Over-expression of Bcl-G$_L$ or Bcl-G$_S$ in cells induced apoptosis, but Bcl-$G_S$ was far more potent than Bcl-$G_L$. Apoptosis induction by Bcl-$G_S$ depended on the BH3 domain, and was suppressed by co-expression of anti-apoptotic Bcl-XL protein. Bcl-XL also co-immunoprecipitated with Bcl-$G_S$ but not with mutants of Bcl-$G_S$ in which the BH3 domain was deleted or mutated and not with Bcl-$G_L$. Bcl-$G_S$ was predominantly localized to cytosolic organelles whereas Bcl-$G_L$ was diffusely distributed throughout the cytosol. The findings suggest that Bcl-$G_L$ is likely in a latent state, whereas the shorter Bcl-$G_S$ protein is constitutively active.

The term "biologically active" or "functional", when used herein as a modifier of an invention Bcl-G, or polypeptide fragment thereof, refers to a polypeptide that exhibits functional characteristics similar to Bcl-G, including those disclosed herein (see Examples I-IX). As disclosed herein, Bcl-G induces apoptosis (see Example IV). Therefore, one function of Bcl-G is a pro-apoptotic function. The pro-apoptotic function of Bcl-G is inhibited by co-expression of the anti-apoptotic protein Bcl-2 (Example IV). Therefore, another function of Bcl-G is modulation by or interaction with an anti-apoptotic protein such as for example, Bcl-2 family member, including Bcl-2 or Bcl-$X_L$, and the like. Bcl-G can function to heterodimerize with a Bcl-2 family member, thereby modulating the apoptotic activity of Bcl-G and/or the Bcl-2 family member. For example, the interaction of BCl-$G_S$ with Bcl-$X_L$ was found to be BH3 domain dependent, and, thus, the pro-apoptotic activity of Bcl-$G_S$ correlates with its ability to bind Bcl-$X_L$ (see Example VI).

Bcl-G is also contemplated herein as having the ability to function as an ion channel. Additionally, Bcl-G is contemplated herein as having the ability to function target to mitochondria, for example, for example, by binding directly to mitochondria or via binding to a protein that is associated with mitochondria such as Bcl-2 or Bcl-$X_L$. Bcl-G can also function to bind adenine nucleotide transporter (ANT) and to other proteins such as voltage-dependent anion channel (VDAC).

Because Bcl-G is located on chromosome 12 in a region that is frequently deleted in cancer cells (Example II) it is contemplated herein that Bcl-G functions as a tumor suppressor. Another functional activity of Bcl-G is the ability to act as an immunogen for the production of polyclonal and monoclonal antibodies that bind specifically to an invention Bcl-G. Thus, an invention nucleic acid encoding Bcl-G will encode a polypeptide specifically recognized by an antibody that also specifically recognizes the Bcl-G protein including the amino acid sequence, set forth in SEQ ID NOS:2, 4 or 42. Such immunologic activity can be assayed by any method known to those of skill in the art. Therefore, Bcl-G functional fragments include polypeptide fragments that function as immunogens for generating a Bcl-G-specific antibody and fragments that specifically bind to a Bcl-G-specific antibody.

Bcl-2 family proteins are central regulators of apoptosis (reviewed in Reed, J. C., *Nature*, 387:773-776 (1997); Adams & Cory, *Science*, 281:1322-1326 (1998); Gross et al., *Genes Dev.*, 13:1899-1911 (1999)). Bcl-2 family proteins are conserved throughout the animal kingdom, with homologues identified in both vertebrates and invertebrates. These proteins contain up to four conserved Bcl-2 Homology (BH) domains, BH1, BH2, BH3, and BH4, which are recognized by their amino-acid sequence similarity. Both anti-apoptotic and pro-apoptotic Bcl-2 family proteins have been identified. These proteins control cell life-death decisions through their effects on events such as mitochondrial release of proteins involved in activation of caspase-family cell death proteases (reviewed in Gross et al., *Genes Dev.*, 13:1899-1911 (1999); Green & Reed, *Science*, 281:1309-1312 (1998); Kroemer & Reed, *Nature Medicine*, 6:513-519 (2000)). Many Bcl-2 family proteins are capable of physically interacting with each other, forming a complex network of homo-and heterodimers, and these physical interactions sometimes play important roles in the opposing effects of pro- and anti-apoptotic members of the family.

The pro-apoptotic members of the Bcl-2 family can be broadly classified into two groups. One group, including Bax, Bak, and Bok in humans, shares structural similarity with the pore-forming domains of certain bacterial toxins and is capable of forming pores in synthetic membranes in vitro (Schendel et al., *Cell Death Differ.*, 5:372-380 (1998); Antonsson et al., *Science*, 277:370-372 (1997); Schlesinger et al., *Proc. Natl. Acad. Sci. USA*, 94:11357-11362 (1997); Shimizu et al., *J Biol Chem.*, 16:12321-12325 (2000)). These protein exhibit cytotoxic effects independently of their ability to bind other Bcl-2 family proteins, including Bcl-2 and other cytoprotective members of the family such as Bcl-$X_L$, Bcl-W, Bfl-1, and Mcl-1. The second group of pro-apoptotic Bcl-2 family proteins varies widely in their amino-acid sequences, often containing only a single region of similarity, the BH3 domain. These "BH3-only" proteins appear to possess no intrinsic or autonomous cytodestructive activity, and instead operate as transdominant inhibitors of the survival proteins. Their antagonism of proteins such as Bcl-2 and Bcl-$X_L$ depends on binding via their BH3 domains to a hydrophobic pocket on target anti-apoptotic proteins (Kelekar & Thompson, *Trends Cell Biol.*, 8:324-330 (1998)).

Gene knock-out studies in mice have demonstrated non-redundant roles for various Bcl-2 family genes in regulating cell life and death in specific tissues or under particular physiological or pathological circumstances (Veis et al., *Cell*, 75:229-240 (1993); Motoyama et al., *Science*, 267:1506-1510 (1995); Knudson et al., *Science*, 270:96-99 (1995); Bouillet et al., *Science*, 286:1735-8 (1999); Yin et al., *Nature*, 400:886-891 (1999)). Thus, it is important to identify all members of the Bcl-2 family and to delineate the cellular contexts in which they contribute to apoptosis regulation. As disclosed herein, a new member of the Bcl-2 family, Bcl-G, has been cloned and characterized.

The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of an invention Bcl-G gene or mRNA transcript in a given sample. The nucleic acid molecules described herein, and fragments thereof, are also useful as primers and/or templates in a PCR reaction for amplifying genes encoding invention proteins described herein.

The term "nucleic acid", also referred to as polynucleotides, encompasses ribonucleic acid (RNA) or deoxyribonucleic acid (DNA), probes, oligonucleotides, and primers and can be single stranded or double stranded. DNA can be either complementary DNA (cDNA) or genomic DNA, and can represent the sense strand, the anti-sense strand or both. Examples of nucleic acids are RNA, cDNA, or isolated genomic DNA encoding an Bcl-G polypeptide. Such nucleic acids include, but are not limited to, nucleic acids comprising substantially the same nucleotide sequence as set forth in SEQ ID NOS:1, 3 or 41. In general, a genomic sequence of the invention includes regulatory regions such as promoters, enhancers, and introns that are outside of the exons encoding a Bcl-G but does not include proximal genes that do not encode Bcl-G.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in any of SEQ ID NOS:2, 4 or 42. In another embodiment, DNA having "substantially the same nucleotide sequence" as the reference nucleotide sequence has at least 60% identity with respect to the reference nucleotide sequence. DNA having substantially the same nucleotide sequence can have at least 70%, at least 90%, or at least 95% identity to the reference nucleotide sequence.

As used herein, a "modification" of a nucleic acid can also include one or several nucleotide additions, deletions, or substitutions with respect to a reference sequence. A modification of a nucleic acid can include substitutions that do not change the encoded amino acid sequence due to the degeneracy of the genetic code. Such modifications can correspond to variations that are made deliberately, or which occur as mutations during nucleic acid replication.

Exemplary modifications of the recited Bcl-G sequences include sequences that correspond to homologs of other species, including mammalian species such as mouse, primates, including monkey and baboon, rat, rabbit, bovine, porcine, ovine, canine, feline, or other animal species. The corresponding Bcl-G sequences of non-human species can be determined by methods known in the art, such as by PCR or by screening genomic, cDNA or expression libraries.

Another exemplary modification of the invention Bcl-G can correspond to splice variant forms of the Bcl-G nucleotide sequence. Additionally, a modification of a nucleotide sequence can include one or more non-native nucleotides, having, for example, modifications to the base, the sugar, or the phosphate portion, or having a modified phosphodiester linkage. Such modifications can be advantageous in increasing the stability of the nucleic acid molecule.

Furthermore, a modification of a nucleotide sequence can include, for example, a detectable moiety, such as a radiolabel, a fluorochrome, a ferromagnetic substance, a luminescent tag or a detectable binding agent such as biotin. Such modifications can be advantageous in applications where detection of a Bcl-G nucleic acid molecule is desired.

The invention also encompasses nucleic acids which differ from the nucleic acids shown in SEQ ID NOS: 1, 3 or 41, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those encoded by the nucleic acids disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding Bcl-G polypeptides that, by virtue of the degeneracy of the genetic code, do not necessarily hybridize to the invention nucleic acids under specified hybridization conditions. As used herein, the term "degenerate" refers to codons that differ in at least one nucleotide from a reference nucleic acid, but encode the same amino acids as the reference nucleic acid. Nucleic acids encoding the invention Bcl-G polypeptides can be comprised of nucleotides that encode substantially the same amino acid sequence as set forth in SEQ ID NOS:2, 4 or 42.

The invention provides an isolated nucleic acid encoding a Bcl-G polypeptide, or a functional fragment thereof. The invention also provides an isolated nucleic acid encoding a Bcl-G polypeptide, or a functional fragment thereof, comprising a nucleic acid selected from:

(a) nucleic acid encoding the amino acid sequence set forth in SEQ ID NOS:2, 4 or 42, or (b) nucleic acid that hybridizes to the nucleic acid of (a) under moderately stringent conditions, wherein said nucleic acid contiguously encodes biologically active Bcl-G, or (c) nucleic acid degenerate with respect to either (a) or (b) above, wherein said nucleic acid encodes biologically active Bcl-G.

In one embodiment, preferred Bcl-G polypeptide include a long form termed Bcl-$G_L$ and a short form termed Bcl-$G_S$. Bcl-$G_L$ contains a BH3 and a BH2 domain, whereas Bcl-$G_S$ contains only a BH3 domain. Bcl-$G_S$ has been found to possess pro-apoptotic activity similar to Bax (see Example III).

Hybridization refers to the binding of complementary strands of nucleic acid, for example, sense:antisense strands or probe:target-nucleic acid to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-nucleic acid to bind a complementary nucleic acid. The hybridized nucleic acids will generally have at least about 60% identity, at least about 75% identity, more at least about 85% identity; or at least about 90% identity. Moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C.

The phrase "high stringency hybridization" refers to conditions that permit hybridization of only those nucleic acid sequences that form stable hybrids in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., *Molecular Cloning: A Laboratory Manual*, 2nd ed., Cold Spring Harbor Press, Plainview, New York (1989); and Ausubel et al., supra, 1999). Nucleic acids encoding polypeptides hybridize under moderately stringent or high stringency conditions to substantially the entire sequence, or substantial portions, for example, typically at least 15-30 nucleotides of the nucleic acid sequence set forth in SEQ ID NOS:1, 3 or 41.

The invention also provides a modification of a Bcl-G nucleotide sequence that hybridizes to a Bcl-G nucleic acid molecule, for example, a nucleic acid molecule referenced as SEQ ID NOS:1, 3 or 41, under moderately stringent conditions. Modifications of Bcl-G nucleotide sequences, where the modification has at least 60% identity to a Bcl-G nucleotide sequence, are also provided. The invention also provides modification of a Bcl-G nucleotide sequence having at least 65% identity, at least 70% identity, at least 75% identity, at least 80% identity, at least 85% identity, at least 90% identity, or at least 95% identity.

Identity of any two nucleic acid sequences can be determined by those skilled in the art based, for example, on a BLAST 2.0 computer alignment, using default parameters. BLAST 2.0 searching is available at
http://www.ncbi.nlm.nih.gov/gorf/bl2.html., as described by Tatiana et al., *FEMS Microbiol Lett.* 174:247-250 (1999); Altschul et al., *Nucleic Acids Res.*, 25:3389-3402 (1997).

One means of isolating a nucleic acid encoding a Bcl-G polypeptide is to probe a cDNA library or genomic library with a natural or artificially designed nucleic acid probe using methods well known in the art. Nucleic acid probes derived from the Bcl-G gene are particularly useful for this purpose. DNA and cDNA molecules that encode Bcl-G polypeptides can be used to obtain complementary genomic DNA, cDNA or RNA from mammals, for example, human, mouse, rat, rabbit, pig, and the like, or other animal sources, or to isolate related cDNA or genomic clones by the screening of cDNA or genomic libraries, by methods well known in the art (see, for example, Sambrook et al., supra, 1989; Ausubel et al., supra, 1999).

The invention additionally provides a nucleic acid that hybridizes under high stringency conditions to the Bcl-G coding portion of any of SEQ ID NOS:1, 3 or 41. The invention also provides a nucleic acid having a nucleotide sequence the same or substantially the same as set that forth in any of SEQ ID NOS:1, 3 or 41.

The invention also provides a method for identifying nucleic acids encoding a mammalian Bcl-G by contacting a sample containing nucleic acids with one or more Bcl-G oligonucleotides, wherein the contacting is effected under high stringency hybridization conditions, and identifying a nucleic acid that hybridizes to the oligonucleotide. The invention additionally provides a method of detecting a Bcl-G nucleic acid molecule in a sample by contacting the sample with two or more Bcl-G oligonucleotides, amplifying a nucleic acid molecule, and detecting the amplification. The amplification can be performed, for example, using PCR. The invention further provides oligonucleotides that function as single stranded nucleic acid primers for amplification of a Bcl-G nucleic acid, wherein the primers comprise a nucleic acid sequence derived from the nucleic acid sequences set forth as SEQ ID NOS:1, 3 or 41.

In accordance with a further embodiment of the present invention, optionally labeled Bcl-G-encoding nucleic acids, or fragments thereof, can be employed to probe a library, for example, a cDNA or genomic library, and the like for additional nucleic acid sequences encoding novel Bcl-G polypeptides. Construction of suitable cDNA libraries is well-known in the art. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 370C, a formamide concentration of about 20%, and a salt concentration of about 5× sodium chloride, sodium citrate_(SSC; 20×SSC contains 3M sodium chloride, 0.3M sodium citrate, pH 7.0). Such conditions will allow the identification of sequences having a substantial degree of similarity with the probe sequence, without requiring perfect identity. The phrase "substantial similarity" refers to sequences which share at least 50% identity. Hybridization conditions are selected which allow the identification of sequences having at least 70% identity with the probe, while discriminating against sequences having a lower degree of identity with the probe. As a result, nucleic acids having substantially the same nucleotide sequence as SEQ ID NOS: 1, 3 or 41 are obtained.

As used herein, a nucleic acid "probe" is single-stranded nucleic acid, or analogs thereof, that has a sequence of nucleotides that includes at least 14, at least 20, at least 50, at least 100, at least 200, at least 300, at least 400, or at least 500 contiguous bases that are the same as or the complement thereof, any contiguous bases set forth in any of SEQ ID NOS:1, 3 or 41. In addition, the entire cDNA encoding region of an invention Bcl-G, or the entire sequence corresponding to SEQ ID NOS:1, 3 or 41 can be used as a probe. Probes can be labeled by methods well-known in the art, as described hereinafter, and used, for example, in various diagnostic kits.

The invention additionally provides a Bcl-G oligonucleotide comprising between 15 and 300 contiguous nucleotides of SEQ ID NOS:1, 3 or 41, or the anti-sense strand thereof. As used herein, the term "oligonucleotide" refers to a nucleic acid molecule that includes at least 15 contiguous nucleotides from a reference nucleotide sequence, can include at least 16, 17, 18, 19, 20 or at least 25 contiguous nucleotides, and often includes at least 30, 40, 50, 60, 70, 80, 90, 100, 125, 150, 175, 200, 225, 250, 275, 300, 325, up to 350 contiguous nucleotides from the reference nucleotide sequence. The reference nucleotide sequence can be the sense strand or the anti-sense strand.

The Bcl-G oligonucleotides of the invention that contain at least 15 contiguous nucleotides of a reference Bcl-G nucleotide sequence are able to hybridize to Bcl-G under moderately stringent hybridization conditions and thus can be advantageously used, for example, as probes to detect Bcl-G DNA or RNA in a sample, and to detect splice variants thereof; as sequencing or PCR primers; as antisense reagents to block transcription of Bcl-G RNA in cells; or in other applications known to those skilled in the art in which hybridization to a Bcl-G nucleic acid molecule is desirable.

It is understood that a Bcl-G nucleic acid molecule, as used herein, specifically excludes previously known nucleic acid molecules consisting of nucleotide sequences having identity with the Bcl-G nucleotide sequence (SEQ ID NOS:1, 3 or 41), such as Expressed Sequence Tags (ESTs), Sequence Tagged Sites (STSs) and genomic fragments, deposited in public databases such as the nr, dbest, dbsts, gss and htgs databases, which are available for searching at http://www.ncbi.nlm.nih.gov/blast/blast.cgi?Jform=0, using the program BLASTN 2.0.9 described by Altschul et al., *Nucleic Acids Res.* 25:3389-3402 (1997).

In particular, a Bcl-G nucleic acid molecule specifically excludes nucleic acid molecules consisting of any of the nucleotide sequences having the Genbank (gb), EMBL (emb) or DDBJ (dbj) accession numbers described below. Similarly, a Bcl-G polypeptide fragment specifically excludes the amino acid fragments encoded by the nucleotide sequences having the GenBank accession numbers described below. GenBank accession numbers specifically excluded include AC005903, AC007439, AW000827, AA399486, AW001213, AI478889, AA400686, AA398276, AI240211, and AA536718. The human BAC referenced as GenBank accession No. AC007537 is also specifically excluded from a Bcl-G nucleic acid.

The isolated Bcl-G nucleic acid molecules of the invention can be used in a variety of diagnostic and therapeutic applications. For example, the isolated Bcl-G nucleic acid molecules of the invention can be used as probes, as described above; as templates for the recombinant expression of Bcl-G polypeptides; or in screening assays such as two-hybrid assays to identify cellular molecules that bind Bcl-G.

Another useful method for producing a Bcl-G nucleic acid molecule of the invention involves amplification of the nucleic acid molecule using PCR and Bcl-G oligonucleotides and, optionally, purification of the resulting product by gel electrophoresis. Either PCR or RT-PCR can be used to produce a Bcl-G nucleic acid molecule having any desired nucleotide boundaries. Desired modifications to the nucleic acid sequence can also be introduced by choosing an appropriate oligonucleotide primer with one or more additions, deletions or substitutions. Such nucleic acid molecules can be amplified exponentially starting from as little as a single gene or mRNA copy, from any cell, tissue or species of interest.

The invention thus provides methods for detecting Bcl-G nucleic acid in a sample. The methods of detecting Bcl-G nucleic acid in a sample can be either qualitative or quantitative, as desired. For example, the presence, abundance, integrity or structure of a Bcl-G can be determined, as desired, depending on the assay format and the probe used for hybridization or primer pair chosen for application.

Useful assays for detecting Bcl-G nucleic acid based on specific hybridization with an isolated Bcl-G nucleic acid molecule are well known in the art and include, for example, in situ hybridization, which can be used to detect altered chromosomal location of the nucleic acid molecule, altered gene copy number, and RNA abundance, depending on the assay format used. Other hybridization assays include, for example, Northern blots and RNase protection assays, which can be used to determine the abundance and integrity of different RNA splice variants, and Southern blots, which can be used to determine the copy number and integrity of DNA. A Bcl-G hybridization probe can be labeled with any suitable detectable moiety, such as a radioisotope, fluorochrome, chemiluminescent marker, biotin, or other detectable moiety known in the art that is detectable by analytical methods.

Useful assays for detecting a Bcl-G nucleic acid in a sample based on amplifying a Bcl-G nucleic acid with two or more Bcl-G oligonucleotides are also well known in the art, and include, for example, qualitative or quantitative polymerase chain reaction (PCR); reverse-transcription PCR (RT-PCR); single strand conformational polymorphism (SSCP) analysis, which can readily identify a single point mutation in DNA based on differences in the secondary structure of single-strand DNA that produce an altered electrophoretic mobility upon non-denaturing gel electrophoresis; and coupled PCR, transcription and translation assays, such as a protein truncation test, in which a mutation in DNA is determined by an altered protein product on an electrophoresis gel. Additionally, the amplified Bcl-G nucleic acid can be sequenced to detect mutations and mutational hot-spots, and specific assays for large-scale screening of samples to identify such mutations can be developed.

The invention further provides an isolated Bcl-G polypeptide, or a functional fragment thereof, encoded by a Bcl-G nucleic acid of the invention. For example, the invention provides a polypeptide comprising the same or substantially the same amino acid sequence as Bcl-$G_L$ (SEQ ID NO:2) or Bcl-$G_S$ (SEQ ID NO:4). Also provided is a Bcl-G polypeptide encoded by a nucleotide sequence comprising the same or substantially the same nucleotide sequence as set forth in SEQ ID NOs:1 or 3. Additionally provided is mouse Bcl-G nucleotide sequence set forth as SEQ ID NO:41 (see Example IX).

Described herein is a new member of the BCL-2 gene family in humans, BCL-G (see Examples I-VIII). The BCL-G gene potentially encodes two protein products, Bcl-$G_L$ and Bcl-$G_S$. Bcl-2 family proteins contain up to four conserved BH domains. The shorter Bcl-$G_S$ protein contains only the BH3 domains, similar to several other pro-apoptotic Bcl-2 family proteins, including Bad, Hrk, Bik, Bim, Apr, and Egl1 (reviewed in Kelekar & Thompson, *Trends Cell Biol.,* 8:324-330 (1998); Reed, J. *Oncogene,* 17:3225-3236 (1998)). In contrast, the longer Bcl-$G_L$ protein contains a BH2 and BH3 domain. No other examples of Bcl-2 family proteins are known which combine BH2 and BH3 domain in the absence of BHI. Though the Bad protein was originally suggested to contain a BH2 domain (Yang et al., *Blood,* 84(Suppl.1):373a-380a (1994)), and has been shown to possess the BH3 domain, inspection of the BH2 region reveals very little similarity of amino-acid sequence with (Ottilie et al., *J. Biol. Chem.,* 272:30866-30872 (1997)) other BH2 domains. In contrast, the BH2 of Bcl-$G_L$ contains a stretch of 8 of 8 residues showing identity or conservative amino-acid substitutions with the BH2 domains of other family members. By comparison, the Bad sequence reveals only 3 of 8 identical or similar amino-acids in the same region. Thus, Bcl-$G_L$ defines a novel structural variant within the Bcl-2 family of apoptosis-regulating proteins.

The production of different protein isoforms by alternative mRNA splicing is a common feature of BCL-2 family genes, including BCL-2, Bcl-X, MCL-1, BAX, and BIM (Tsujimoto & Croce, *Proc. Natl. Acad. Sci. USA,* 83:5214-5218 (1986); O'Connor et al., *EMBO J.,* 17:384-395 (1998); Boise et al., *Cell,* 74:597-608 (1993); Oltvai et al., *Cell,* 74:609-619 (1993); Bingle et al., *J. Biol. Chem.,* 275:22136-22146 (2000)). Unlike BCL-X, which encodes a longer and short protein, Bcl-$X_L$ and Bcl-$X_S$, possessing anti-apoptotic and pro-apoptotic functions, respectively, the longer isoform of Bcl-G did not display anti-apoptotic activity. When overexpressed, Bcl-$G_L$ induced modest and variable increases in apoptosis, whereas the shorter Bcl-$G_S$ protein consistently exhibited potent cytotoxic activity. This behavior is reminiscent of the proteins encoded by the BIM gene, which include Bim-short (Bim$_S$), Bim-long (Bim$_L$) and Bim-Extra-Long (Bim$_{EL}$) (O'Connor et al., *EMBO J.,* 17:384-395 (1998)). The longer proteins, Bim$_L$ and Bim$_{EL}$, are sequestered in complexes with dynein light-chain (DLC) in association with microtubules, thus preventing them from interacting with target proteins such as Bcl-X$_L$ on the surface of mitochondria and other organelles (Puthalakath et al., *Mol. Cell,* 3:287-96 (1999)). In contrast, because the shortest isoform, Bim$_S$, does not associate with DLC, it is free to interact with Bcl-X$_L$, Bcl-2, and other survival proteins and hence displays far more potent apoptotic activity when over-expressed in cells. By analogy, the longer Bcl-G$_L$ protein could be sequestered in an inactive complex with an unidentified protein.

Besides interactions with sequestering proteins, the activity of pro-apoptotic Bcl-2 family proteins can be suppressed by other mechanisms, including post-translational modifications. For example, the Bad protein is inactivated by phosphorylation. This protein can be directly or indirectly phosphorylated by several protein kinases, including PKA, PKB (Akt), Raf1, and Pak1, thus preventing it from dimerizing with target proteins such as Bcl-2 and Bcl-X$_L$ (reviewed in Reed, J. *Oncogene,* 17:3225-3236 (1998); Datta et al., *Genes Dev.,* 13:2905-2927 (1999)). The intracellular location of Bad varies, depending on its phosphorylation state, with phosphorylated Bad residing in the cytosol and unphosphorylated Bad associated with mitochondria and other intracellular organelles where Bcl-2 and Bcl-X$_L$ are located. In this regard, the Bcl-G$_L$ protein contains candidate phosphorylation sites for protein kinase A (PKA) and protein kinase C (PKC), including some not found in Bcl-G$_S$. However, in vivo phosphorylation of Bcl-G$_L$ has not been observed in pilot experiments.

Another post-translational modification shown previously to activate latent pro-apoptotic Bcl-2 family proteins is proteolysis. Specifically, the Bid protein contains a N-terminal domain of ~56 amino-acids that masks its BH3 domain, reducing its ability to dimerize with other Bcl-2 family proteins. Upon cleavage by caspases, however, removal of the N-terminal domain exposes the BH3 domain and is associated with translocation of Bid from the cytosol to mitochondria, where it induces cytochrome c release and apoptosis (Li et al., *Cell,* 94:491-501 (1998); Luo et al., *Cell,* 94:481-490 (1998)). While Bcl-G$_L$ contains candidate caspase recognition sites, no significant cleavage of Bid has been observed in vitro using purified active caspases or in cells during apoptosis. It is possible, however, that a specific caspase not yet tested is capable of cleaving and activating Bcl-G$_L$.

Though possessing no hydrophobic region that might anchor it in membranes, the Bcl-G$_S$ protein was constitutively associated with intracellular organelles. Interestingly, removal of the BH3 domain did not interfere with organellar-targeting of Bcl-G$_S$, but did abolish dimerization with Bcl-X$_L$. Thus, the BH3 domain apparently is not responsible for association of Bcl-G$_S$ with intracellular organelles. This BH3-independent targeting of Bcl-G$_S$ differs from some other "BH3-only" Bcl-2 family proteins such as Bad, where it has been observed that removal of the BH3 domain abrogates binding to anti-apoptotic Bcl-2 family proteins as well as association with mitochondria (Zha et al., *J. Biol. Chem.,* 272:24101-24104 (1997)).

The BCL-G gene resides on chromosome 12p12, a region deleted in ~50% of prostate cancers, ~30% of ovarian cancers, and ~30% of childhood acute lymphocytic leukemias (ALLs) (Kibel et al., *J Urol.,* 1:192-196 (2000); Aissani et al., *Leuk Lymphoma,* 34:231-239 (1999); Hatta et al., *Br J Cancer,* 75:1256-1262 (1997)). Given that at least one of the protein products of the BCL-G gene exhibits pro-apoptotic function, it is possible that BCL-G represents a tumor suppressor gene. However, thus far, somatic mutations in the exons of BCL-G have not been detected nor evidence of deletion of both BCL-G alleles in tumor cell lines or primary tumor specimens tested so far. Further studies are required therefore to determine whether loss of BCL-G expression occurs in tumors by means other than somatic alterations in gene structure and DNA sequence, such as changes in gene methylation or aberrant transcriptional or post-transcriptional regulation.

Investigation of the tissue-distribution of Bcl-G$_L$ and Bcl-G$_S$ mRNAs by RT-PCR revealed that Bcl-G$_L$ mRNA is found in several normal adult tissues, whereas Bcl-G$_S$ was detected only in testis. This finding indicates tissue-specific regulation of Bcl-G$_S$ mRNA splicing. Tissue-specific splicing of other Bcl-2 family mRNAs has been observed previously. For example, Bcl-X mRNA splicing events which generate the pro-apoptotic Bcl-X$_S$ protein occur in the thymus during T-cell ontogeny and in the mammary gland during post-lactation involution, in association with extensive apoptosis induction (Boise et al., *Cell,* 74:597-608 (1993); Heermeier et al., *Mech. Dev.,* 56:197-207 (1996)). Additional studies are performed to assess differential mRNA splicing patterns of Bcl-G transcripts during fetal development and following various scenarios in the adult where apoptosis occurs as part of a normal physiological response or an abnormal pathological reaction to environmental insults.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptides, or encoding nucleic acids, containing less than the described levels of sequence identity arising as splice variants or that are modified by conservative amino acid substitutions, or by substitution of degenerate codons are also encompassed within the scope of the present invention.

Also encompassed by the term Bcl-G are functional fragments or polypeptide analogs thereof. The term "functional fragment" refers to a peptide fragment that is a portion of a full length Bcl-G protein, provided that the portion has a biological activity, as defined herein, that is characteristic of the corresponding full length protein. Thus, the invention also provides functional fragments of invention Bcl-G proteins, which can be identified using the binding and routine methods, such as bioassays described herein. A Bcl-G polypeptide functional fragment can be a BH3 or BH2 domain, for example, a BH3 domain referenced as SEQ ID NOS:5 or 9 or a BH2 domain referenced as SEQ ID NOS:6 or 18. The BH3 domain of Bcl-G is 33% identical to the BH3 domain of Bcl-2, 44% identical to the BH3 domain of Bcl-X$_L$, and 66% identical to the BH3 domain of Bax.

In addition, a functional fragment of a Bcl-G polypeptide can be Bax homology region. A region upstream of the BH3 domain shares a high degree of homology with Bax, including a 12 amino acid residue motif that is 70% identical between Bcl-G and Bax. Therefore, such a Bax homology region can function similarly to Bax, for example, as a possible binding domain. The N-terminal 150 amino acids of Bcl-G are not similar to any known amino acid sequence available in public databases. Therefore, the N-terminal region of Bcl-G can function as Bcl-G-specific functional domain that confers a biological activity that is specific for Bcl-G relative to other members of the Bcl-2 family.

The invention also provides a chimeric protein comprising a domain selected from the group consisting of BH3 (SEQ ID NOS:5 or 9) and BH2 (SEQ ID NOS:6 or 18). A chimeric protein comprising a Bcl-G functional domain can be generated, for example, by recombinantly expressing a Bcl-G domain such as BH2 or BH3 fused to another polypeptide. Alternatively, the Bcl-G functional domain can be expressed as a fusion to another polypeptide.

In another embodiment of the invention, Bcl-G-containing chimeric proteins are provided comprising an invention Bcl-G, or fragments thereof, having the sequence of SEQ ID NO:2, SEQ ID NO:4, or SEQ ID NO:42, and further comprising one or more sequences from a heterologous protein. Sequences from heterologous proteins with which the Bcl-G or functional fragment thereof are fused can include, for example, glutathione-S-transferase, an antibody, or other proteins or functional fragments thereof which facilitate recovery of the chimera. Further proteins with which the Bcl-G or functional fragment thereof are fused will include, for example, luciferase, green fluorescent protein, an antibody, or other proteins or functional fragments thereof which facilitate identification of the chimera. Still further proteins with which the Bcl-G or functional fragment thereof are fused will include, for example, the LexA DNA binding domain, ricin, α-sarcin, an antibody, or other proteins which have therapeutic properties or other biological activity.

As such chimeric proteins include sequences from two different proteins, the resultant amino acid sequence of the chimeric protein will typically be a non-naturally occurring sequence. Thus, in accordance with this embodiment of the invention, there are provided chimeric proteins comprising an invention Bcl-G, or fragments thereof, having the sequence of SEQ ID NO:2, SEQ ID NO:4, or SEQ ID NO:42, or a fragment thereof, provided the sequence of the chimeric protein is not naturally occurring.

In another embodiment of the invention, there are provided hetero-oligomers comprising invention Bcl-G polypeptides and fragments thereof, invention Bcl-G-containing proteins, Bcl-G-containing chimeric proteins, or combinations thereof. As disclosed herein, Bcl-G contains a BH3 domain, which functions as a ligand to bind Bcl-2 family members (Example I). Bcl-G can function to bind Bcl-2 family members. Thus, hetero-oligomers comprising invention Bcl-G polypeptides (SEQ ID NOS:2, 4 or 42) and fragments thereof, invention Bcl-G-containing proteins, Bcl-G-containing chimeric proteins, or combinations thereof, and further comprising Bcl-2 family members such as Bcl-2, Bcl-$X_L$ or other Bcl-2 family members are provided.

As used herein, the term "polypeptide" when used in reference to Bcl-G is intended to refer to a peptide or polypeptide of two or more amino acids. The term "polypeptide analog" includes any polypeptide having an amino acid residue sequence substantially the same as a sequence specifically described herein in which one or more residues have been conservatively substituted with a functionally similar residue and which displays the ability to functionally mimic a Bcl-G as described herein. A "modification" of a Bcl-G polypeptide also encompasses conservative substitutions of a Bcl-G polypeptide amino acid sequence. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are included within Bcl-G polypeptides so long as the polypeptide retains some or all of its function as described herein.

The amino acid length of functional fragments or polypeptide anlogs of the present invention can range from about 5 amino acids up to the full-length protein sequence of an invention Bcl-G. In certain embodiments, the amino acid lengths include, for example, at least about 10 amino acids, at least about 15, at least about 20, at least about 25, at least about 30, at least about 35, at least about 40, at least about 45, at least about 50, at least about 75, at least about 100, at least about 150, at least about 200, at least about 250 or more amino acids in length up to the full-length Bcl-G protein sequence. The functional fragments can be contiguous amino acid sequences of a Bcl-G polypeptide, including contiguous amino acid sequences of SEQ ID NOS:2, 4 or 42.

A modification of a polypeptide can also include derivatives, analogues and functional mimetics thereof, provided that such polypeptide displays the Bcl-G biological activity. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds. Polypeptides of the present invention also include any polypeptide having one or more additions and/or deletions of residues, relative to the sequence of a polypeptide whose sequence is shown herein, so long as Bcl-G activity is maintained.

A modification of a Bcl-G polypeptide includes functional mimetics thereof. Mimetics encompass chemicals containing chemical moieties that mimic the function of the polypeptide. For example, if a polypeptide contains two charged chemical moieties having functional activity, a mimetic places two charged chemical moieties in a spatial orientation and constrained structure so that the charged chemical function is maintained in three-dimensional space. Thus, a mimetic, which orients functional groups that provide a function of Bcl-G, are included within the meaning of a Bcl-G derivative. All of these modifications are included within the term "polypeptide" so long as the Bcl-G polypeptide or functional fragment retains its function.

The invention provides an isolated Bcl-G polypeptide, or functional fragment thereof. The invention Bcl-G polypeptides can be isolated by a variety of methods well-known in the art, for example, recombinant expression systems described herein, precipitation, gel filtration, ion-exchange, reverse-phase and affinity chromatography, and the like. Other well-known methods are described in Deutscher et al., *Guide to Protein Purification: Methods in Enzymology Vol. 182*, (Academic Press, (1990)). Alternatively, the isolated polypeptides of the present invention can be obtained using well-known recombinant methods (see, for example, Sambrook et al., supra, 1989; Ausubel et al., supra, 1999). The methods and conditions for biochemical purification of a polypeptide of the invention can be chosen by those skilled in the art, and purification monitored, for example, by an immunological assay or a functional assay.

An example of the means for preparing the invention polypeptide(s) is to express nucleic acids encoding Bcl-G in a suitable host cell, such as a bacterial cell, a yeast cell, an amphibian cell such as an oocyte, or a mammalian cell, using methods well known in the art, and recovering the expressed polypeptide, again using well-known purification methods, so described herein. Invention polypeptides can be isolated directly from cells that have been transformed with expression vectors as described herein. Recombinantly expressed polypeptides of the invention can also be expressed as fusion proteins with appropriate affinity tags, such as glutathione S transferase (GST) or poly His, and affinity purified. The invention polypeptide, biologically functional fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Bcl-G polypeptides can be administered to an individual to increase an activity associated with a Bcl-G polypeptide, including induction of apoptosis or functioning as a tumor suppressor. For example, a Bcl-G polypeptide can be administered therapeutically to an individual using expression vectors containing nucleic acids encoding Bcl-G polypeptides, as described below. In addition, Bcl-G polypeptides, or a functional portion thereof, can be directly administered to an individual. Methods of administering therapeutic polypeptides are well known to those skilled in the art, for example, as a pharmaceutical composition.

In a particular embodiment, a Bcl-G polypeptide, or functional fragment thereof, can be administered to an individual so that the Bcl-G polypeptide or functional fragment is targeted to a tumor to induce apoptosis or otherwise function as a tumor suppressor. One method of delivering a Bcl-G polypeptide to an intracellular target is to fuse a Bcl-G polypeptide or functional fragment to an intracellular-targeting peptide that can penetrate the cell membrane or otherwise deliver a polypeptide to the intracellular environment such as via internalization, thereby causing the fused Bcl-G polypeptide to enter the cell. One example of such an intracellular-targeting peptides is a fusion to the transduction domain of HIV TAT, which allows transduction of up to 100% of cells (Schwarze et al., *Science* 285:1569-1572 (1999); Vocero-Akbani et al., *Nature Med.* 5:29-33 (1999)).

Another example of such an intracellular-targeting peptide is the Antennapeida homeoprotein internalization domain (Holinger et al., *J. Biol. Chem.* 274:13298-13304 (1999)). Still another intracellular-targeting peptide is a peptide that is specific for a cell surface receptor, which allows binding and internalization of a fusion polypeptide via receptor-mediated endocytosis (Ellerby et al., *Nature Med.* 5:1032-1038 (1999)). Such intracellular-targeting peptides that mediate specific receptor interactions can be advantageously used to target a tumor (see Ellerby et al., supra, 1999). Alternatively, a Bcl-G polypeptide of the invention can be incorporated, if desired, into liposomes, microspheres or other polymer matrices (Gregoriadis, *Liposome Technoloqy, Vols. I to III*, 2nd ed., CRC Press, Boca Raton Fla. (1993)).

The invention additionally provides a method for modulating the activity of an oncogenic polypeptide by contacting the oncogenic polypeptide with a substantially pure Bcl-G, or an oncogenic protein-binding fragment thereof. Bcl-G can function to bind oncogenic proteins such as Bcl-2. Therefore, Bcl-G or functional fragments that bind to an oncogenic protein such as Bcl-2 can be used to modulate the activity of the oncogenic protein.

The present invention also provides compositions containing an acceptable carrier and any of an isolated, purified Bcl-G mature protein or functional polypeptide fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil and water emulsion, and various types of wetting agents.

The invention thus provides a therapeutic composition comprising a pharmaceutically acceptable carrier and a compound selected from the group consisting of a Bcl-G polypeptide, a functional fragment of Bcl-G, a Bcl-G modulating compound, and an anti-Bcl-G antibody. The invention additionally provides a method of treating a pathology characterized by abnormal cell proliferation by administering an effective amount of the composition containing a pharmaceutically acceptable carrier and a compound selected from the group consisting of a Bcl-G polypeptide, a functional fragment of Bcl-G, a Bcl-G modulating compound, and an anti-Bcl-G antibody.

Also provided are antisense-nucleic acids having a sequence capable of binding specifically with full-length or any portion of an mRNA that encodes Bcl-G polypeptides so as to prevent translation of the mRNA. The antisense-nucleic acid can have a sequence capable of binding specifically with any portion of the sequence of the cDNA encoding Bcl-G polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense-nucleic acid is an antisense-nucleic acid comprising chemical analogs of nucleotides.

The present invention provides means to modulate levels of expression of Bcl-G polypeptides by recombinantly expressing Bcl-G anti-sense nucleic acids or employing synthetic anti-sense nucleic acid compositions (hereinafter SANC) that inhibit translation of mRNA encoding these polypeptides. Synthetic oligonucleotides, or other antisense-nucleic acid chemical structures designed to recognize and selectively bind to mRNA are constructed to be complementary to full-length or portions of an Bcl-G coding strand, including nucleotide sequences set forth in SEQ ID NOS:1, 3 or 41.

The SANC is designed to be stable in the blood stream for administration to a subject by injection, or in laboratory cell culture conditions. The SANC is designed to be capable of passing through the cell membrane in order to enter the cytoplasm of the cell by virtue of physical and chemical properties of the SANC, which render it capable of passing through cell membranes, for example, by designing small, hydrophobic SANC chemical structures, or by virtue of specific transport systems in the cell which recognize and transport the SANC into the cell. In addition, the SANC can be designed for administration only to certain selected cell populations by targeting the SANC to be recognized by specific cellular uptake mechanisms which bind and take up the SANC only within select cell populations. In a particular embodiment the SANC is an antisense oligonucleotide.

For example, the SANC may be designed to bind to a receptor found only in a certain cell type, as discussed above. The SANC is also designed to recognize and selectively bind to target mRNA sequence, which can correspond to a sequence contained within the sequences shown in SEQ ID NOS:1, 3 or 41. The SANC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify ithe target mRNA. SANCs have been shown to be capable of such properties when directed against mRNA targets (see Cohen et al., TIPS, 10:435 (1989) and Weintraub, Sci. American, January (1990), pp.40).

The invention further provides a method of modulating the level of apoptosis in a cell by introducing an antisense nucleotide sequence into the cell, wherein the antisense nucleotide sequence specifically hybridizes to a nucleic acid molecule encoding a Bcl-G, wherein the hybridization reduces or inhibits the expression of the Bcl-G in the cell. The use of anti-sense nucleic acids, including recombinant anti-sense nucleic acids or SANCs, can be advantageously used to inhibit cell death.

Compositions comprising an amount of the antisense-nucleic acid of the invention, effective to reduce expression of Bcl-G polypeptides by entering a cell and binding specifically to mRNA encoding Bcl-G polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. For example, the structure can be part of a protein known to bind to a cell-type specific receptor such as a tumor.

Antisense-nucleic acid compositions are useful to inhibit translation of mRNA encoding invention polypeptides. Synthetic oligonucleotides, or other antisense chemical structures are designed to bind to mRNA encoding Bcl-G polypeptides and inhibit translation of mRNA and are useful as compositions to inhibit expression of Bcl-G associated genes in a tissue sample or in a subject.

The invention also provides a method for expression of a Bcl-G polypeptide by culturing cells containing a Bcl-G nucleic acid under conditions suitable for expression of Bcl-G. Thus, there is provided a method for the recombinant production of a Bcl-G of the invention by expressing the nucleic acid sequences encoding Bcl-G in suitable host cells. Recombinant DNA expression systems that are suitable to produce Bcl-G described herein are well-known in the art (see, for example, Ausubel et al., supra, 1999). For example, the above-described nucleotide sequences can be incorporated into vectors for further manipulation. As used herein, vector refers to a recombinant DNA or RNA plasmid or virus containing discrete elements that are used to introduce heterologous DNA into cells for either expression or replication thereof.

The invention also provides vectors containing the Bcl-G nucleic acids of the invention. Suitable expression vectors are well-known in the art and include vectors capable of expressing nucleic acid operatively linked to a regulatory sequence or element such as a promoter region or enhancer region that is capable of regulating expression of such nucleic acid. Appropriate expression vectors include those that are replicable in eukaryotic cells and/or prokaryotic cells and those that remain episomal or those which integrate into the host cell genome.

Promoters or enhancers, depending upon the nature of the regulation, can be constitutive or regulated. The regulatory sequences or regulatory elements are operatively linked to a nucleic acid of the invention such that the physical and functional relationship between the nucleic acid and the regulatory sequence allows transcription of the nucleic acid.

Suitable vectors for expression in prokaryotic or eukaryotic cells are well known to those skilled in the art (see, for example, Ausubel et al., supra, 1999). Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. The vectors of the invention are useful for subcloning and amplifying a Bcl-G nucleic acid molecule and for recombinantly expressing a Bcl-G polypeptide. A vector of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell.

The invention additionally provides recombinant cells containing Bcl-G nucleic acids of the invention. The recombinant cells are generated by introducing into a host cell a vector containing a Bcl-G nucleic acid molecule. The recombinant cells are transducted, transfected or otherwise genetically modified. Exemplary host cells that can be used to express recombinant Bcl-G molecules include mammalian primary cells; established mammalian cell lines, such as COS, CHO, HeLa, NIH3T3, HEK 293 and PC12 cells; amphibian cells, such as Xenopus embryos and oocytes; and other vertebrate cells. Exemplary host cells also include insect cells such as *Drosophila*, yeast cells such as *Saccharomyces cerevisiae, Saccharomiyces pombe*, or *Pichia pastoris*, and prokaryotic cells such as *Escherichia coli*.

In one embodiment, nucleic acids encoding the invention Bcl-G polypeptides can be delivered into mammalian cells, either in vivo or in vitro using suitable vectors well-known in the art. Suitable vectors for delivering a Bcl-G polypeptide, or a functional fragment thereof to a mammalian cell, include viral vectors such as retroviral vectors, adenovirus, adeno-associated virus, lentivirus, herpesvirus, as well as non-viral vectors such as plasmid vectors. Such vectors are useful for providing therapeutic amounts of a Bcl-G polypeptide (see, for example, U.S. Pat. No. 5,399,346, issued Mar. 21, 1995). Delivery of Bcl-G polypeptides or nucleic acids therapeutically can be particularly useful when targeted to a tumor cell, thereby inducing apoptosis in tumor cells. In addition, where it is desirable to limit or reduce the in vivo expression of the invention Bcl-G, the introduction of the antisense strand of the invention nucleic acid is contemplated.

Viral based systems provide the advantage of being able to introduce relatively high levels of the heterologous nucleic acid into a variety of cells. Suitable viral vectors for introducing invention nucleic acid encoding an Bcl-G protein into mammalian cells are well known in the art. These viral vectors include, for example, Herpes simplex virus vectors (Geller et al., *Science,* 241:1667-1669 (1988)); vaccinia virus vectors (Piccini et al., *Meth. Enzymology,* 153:545-563 (1987)); cytomegalovirus vectors (Mocarski et al., in *Viral*

Vectors, Y. Gluzman and S. H. Hughes, Eds., Cold Spring Harbor Laboratory, Cold Spring Harbor, N.Y., 1988, pp. 78-84)); Moloney murine leukemia virus vectors (Danos et_al., *Proc. Natl. Acad. Sci. USA*, 85:6460-6464 (1988); Blaese et al., *Science*, 270:475-479 (1995); Onodera et al., *J. Virol.*, 72:1769-1774 (1998)); adenovirus vectors (Berkner, *Biotechniques*, 6:616-626 (1988); Cotten et al., *Proc. Natl. Acad. Sci. USA*, 89:6094-6098 (1992); Graham et al., *Meth. Mol. Biol.*, 7:109-127 (1991); Li et al., *Human Gene Therapy*, 4:403-409 (1993); Zabner et al., *Nature Genetics*, 6:75-83 (1994)); adeno-associated virus vectors (Goldman et al., *Human Gene Therapy*, 10:2261-2268 (1997); Greelish et al., *Nature Med.*, 5:439-443 (1999); Wang et al., *Proc. Natl. Acad. Sci. USA*, 96:3906-3910 (1999); Snyder et al., *Nature Med.*, 5:64-70 (1999); Herzog et al., *Nature Med.*, 5:56-63 (1999)); retrovirus vectors (Donahue et al., *Nature Med.*, 4:181-186 (1998); Shackleford et al., *Proc. Natl. Acad. Sci. USA*, 85:9655-9659 (1988); U.S. Pat. Nos. 4,405,712, 4,650, 764 and 5,252,479, and WIPO publications WO 92/07573, WO 90/06997, WO 89/05345, WO 92/05266 and WO 92/14829; and lentivirus vectors (Kafri et al., *Nature Genetics*, 17:314-317 (1997)).

For example, in one embodiment of the present invention, adenovirus-transferrin/polylysine-DNA (TfAdpl-DNA) vector complexes (Wagner et al., *Proc. Natl. Acad. Sci., USA*, 89:6099-6103 (1992); Curiel et al., *Hum. Gene Ther.*, 3:147-154 (1992); Gao et al., *Hum. Gene Ther.*, 4:14-24 (1993)) are employed to transduce mammalian cells with heterologous Bcl-G nucleic acid. Any of the plasmid expression vectors described herein may be employed in a TfAdpl-DNA complex.

Vectors useful for therapeutic administration of a Bcl-G polypeptide of nucleic acid can contain a regulatory element that provides tissue specific or inducible expression of an operatively linked nucleic acid. One skilled in the art can readily determine an appropriate tissue-specific promotor or enhancer that allows exparssion of a Bcl-G polypeptide or nucleic acid in a desired tissue. Any of a variety of inducible promoters or enhancers can also be included in the vector for regulatable expression of a Bcl-G polypeptide or nucleic acid. Such inducible systems, include, for example, tetracycline inducible system (Gossen & Bizard, *Proc. Natl. Acad. Sci. USA*, 89:5547-5551 (1992); Gossen et al., *Science*, 268:1766-1769 (1995); Clontech, Palo Alto, Calif.); metalothionein promoter induced by heavy metals; insect steroid hormone responsive to ecdysone or related steroids such as muristerone (No et al., *Proc. Natl. Acad. Sci. USA*, 93:3346-3351 (1996); Yao et al., *Nature*, 366:476-479 (1993); Invitrogen, Carlsbad, Calif.); mouse mammory tumor virus (MMTV) induced by steroids such as glucocortocoid and estrogen (Lee et al., Nature, 294:228-232 (1981); and heat shock promoters inducible by temperature changes.

An inducible system particularly useful for therapeutic administration utilizes an inducible promotor that can be regulated to deliver a level of therapeutic product in response to a given level of drug administered to an individual and to have little or no expression of the therapeutic product in the absence of the drug. One such system utilizes a Gal4 fusion that is inducible by an antiprogestin such as mifepristone in a modified adenovirus vector (Burien et al., *Proc. Natl. Acad. Sci. USA*, 96:355-360 (1999). Another such inducible system utilizes the drug rapamycin to induce reconstitution of a transcriptional activator containing rapamycin binding domains of FKBP12 and FRAP in an adeno-associated virus vector (Ye et al., *Science*, 283:88-91 (1999)). It is understood that any combination of an inducible system can be combined in any suitable vector, including those disclosed herein. Such a regulatable inducible system is advantageous because the level of expression of the therapeutic product can be controlled by the amount of drug administered to the individual or, if desired, expression of the therapeutic product can be terminated by stopping administration of the drug.

The invention additionally provides an isolated anti-Bcl-G antibody having specific reactivity with a Bcl-G. The anti-Bcl-G antibody can be a monoclonal antibody or a polyclonal antibody. The invention further provides cell lines producing monoclongal antibodies having specific reactivity with a Bcl-G.

The invention thus provides antibodies that specifically bind a Bcl-G polypeptide. As used herein, the term "antibody" is used in its broadest sense to include polyclonal and monoclonal antibodies, as well as antigen binding fragments of such antibodies. With regard to an anti-Bcl-G antibody of the invention, the term "antigen" means a native or synthesized Bcl-G polypeptide or fragment thereof. An anti-Bcl-G antibody, or antigen binding fragment of such an antibody, is characterized by having specific binding activity for a Bcl-G polypeptide or a peptide portion thereof of at least about $1 \times 10^5$ $M^{-1}$. Thus, Fab, F(ab')$_2$, Fd and Fv fragments of an anti-Bcl-G antibody, which retain specific binding activity for a Bcl-G polypeptide, are included within the definition of an antibody. Specific binding activity of a Bcl-G polypeptide can be readily determined by one skilled in the art, for example, by comparing the binding activity of an anti-Bcl-G antibody to a Bcl-G polypeptide versus a control polypeptide that is not a Bcl-G polypeptide. Methods of preparing polyclonal or monoclonal antibodies are well known to those skilled in the art (see, for example, Harlow and Lane, *Antibodies: A Laboratory Manual*, Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al. (*Science* 246:1275-1281 (1989)). These and other methods of making, for example, chimeric, humanized, CDR-grafted, single chain, and bifunctional antibodies are well known to those skilled in the art (Winter and Harris, *Immunol. Today* 14:243-246 (1993); Ward et al., *Nature* 341:544-546 (1989); Harlow and Lane, supra, 1988); Hilyard et al., *Protein Engineerinq: A practical approach* (IRL Press 1992); Borrabeck, *Antibody Enoineering*, 2d ed. (Oxford University Press 1995)).

Anti-Bcl-G antibodies can be raised using a Bcl-G immunogen such as an isolated Bcl-G polypeptide having the amino acid sequence of SEQ ID NOS:2, 4 or 42, or a fragment thereof, which can be prepared from natural sources or produced recombinantly, or a peptide portion of the Bcl-G polypeptide. Such peptide portions of a Bcl-G polypeptide are functional antigenic fragments if the antigenic peptides can be used to generate a Bcl-G-specific antibody. A non-immunogenic or weakly immunogenic Bcl-G polypeptide or portion thereof can be made immunogenic by coupling the hapten to a carrier molecule such as bovine serum albumin (BSA) or keyhole limpet hemocyanin (KLH). Various other carrier molecules and methods for coupling a hapten to a carrier molecule are well known in the art (see, for example, Harlow and Lane, supra, 1988). An immunogenic Bcl-G polypeptide fragment can also be generated by expressing the peptide portion as a fusion protein, for example, to glutathione S transferase (GST), polyHis or the like. Methods for expressing peptide fusions are well known to those skilled in the art (Ausubel et al., *Current Protocols in Molecular Biology* (Supplement 47), John Wiley & Sons, New York (1999)).

The invention further provides a method for detecting the presence of a human Bcl-G in a sample by contacting a sample with a Bcl-G-specific antibody, and detecting the presence of specific binding of the antibody to the sample, thereby detecting the presence of a human Bcl-G in the sample. Bcl-G specific antibodies can be used in diagnostic methods and systems to detect the level of Bcl-G present in a sample. As used herein, the term "sample" is intended to mean any biological fluid, cell, tissue, organ or portion thereof, that includes or potentially includes Bcl-G nucleic acids or polypeptides. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid or protein preparation.

Bcl-G-specific antibodies can also be used for the immunoaffinity or affinity chromatography purification of the invention Bcl-G. In addition, methods are contemplated herein for detecting the presence of an invention Bcl-G protein in a cell, comprising contacting the cell with an antibody that specifically binds to Bcl-G polypeptides under conditions permitting binding of the antibody to the Bcl-G polypeptides, detecting the presence of the antibody bound to the Bcl-G polypeptide, and thereby detecting the presence of invention polypeptides in a cell. With respect to the detection of such polypeptides, the antibodies can be used for in vitro diagnostic or in vivo imaging methods.

Immunological procedures useful for in vitro detection of target Bcl-G polypeptides in a sample include immunoassays that employ a detectable antibody. Such immunoassays include, for example, immunohistochemistry, immunofluorescence, ELISA assays, radioimmunoassay, FACS analysis, immunoprecipitation, immunoblot analysis, Pandex microfluorimetric assay, agglutination assays, flow cytometry and serum diagnostic assays, which are well known in the art (Harlow and Lane, supra, 1988; Harlow and Lane, *Using Antibodies: A Laboratory Manual*, Cold Spring Harbor Press (1999)).

An antibody can be made detectable by various means well known in the art. For example, a detectable marker can be directly attached to the antibody or indirectly attached using, for example, a secondary agent that recognizes the Bcl-G specific antibody. Useful markers include, for example, radionucleotides, enzymes, binding proteins such as biotin, fluorogens, chromogens and chemiluminescent labels.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189-231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.*, 73:3-46 (1981). Conventional means of protein conjugation or coupling by activated functional groups are particularly applicable. See, for example, Aurameas et al., *Scand. J. Immunol.*, Vol. 8, Suppl. 7:7-23 (1978), Rodwell et al., *Biotech.*, 3:889-894 (1984), and U.S. Pat. No. 4,493,795.

In addition to detecting the presence of a Bcl-G polypeptide, invention anti-Bcl-G antibodies are contemplated for use herein to modulate the activity of the Bcl-G polypeptide in living animals, in humans, or in biological tissues or fluids isolated therefrom. The term "modulate" refers to a compound's ability to increase the biological activity by functioning as an agonist or inhibit the biological activity by functioning as an antagonist of an invention Bcl-G polypeptide. Accordingly, compositions comprising a carrier and an amount of an antibody having specificity for Bcl-G polypeptides effective to block naturally occurring ligands or other Bcl-G-binding proteins from binding to invention Bcl-G polypeptides are contemplated herein. For example, a monoclonal antibody directed to an epitope of an invention Bcl-G polypeptide, including an amino acid sequence set forth in SEQ ID NOS:2, 4 or 42, can be useful for this purpose.

The present invention further provides transgenic non-human mammals that are capable of expressing exogenous nucleic acids encoding Bcl-G polypeptides. As employed herein, the phrase "exogenous nucleic acid" refers to nucleic acid sequence which is not native to the host, or which is present in the host in other than its native environment, for example, as part of a genetically engineered DNA construct. In addition to naturally occurring levels of Bcl-G, a Bcl-G polypeptide of the invention can either be overexpressed or underexpressed in transgenic mammals, for example, underexpressed in a knock-out animal.

Also provided are transgenic non-human mammals capable of expressing nucleic acids encoding Bcl-G polypeptides so mutated as to be incapable of normal activity. Therefore, the transgenic non-human mammals do not express native Bcl-G or have reduced expression of native Bcl-G. The present invention also provides transgenic non-human mammals having a genome comprising antisense nucleic acids complementary to nucleic acids encoding Bcl-G polypeptides, placed so as to be transcribed into antisense mRNA complementary to mRNA encoding Bcl-G polypeptides, which hybridizes to the mRNA and, thereby, reduces the translation thereof. The nucleic acid can additionally comprise an inducible promoter and/or tissue specific regulatory elements, so that expression can be induced, or restricted to specific cell types.

Animal model systems useful for elucidating the physiological and behavioral roles of Bcl-G polypeptides are also provided, and are produced by creating transgenic animals in which the expression of the Bcl-G polypeptide is altered using a variety of techniques. Examples of such techniques include the insertion of normal or mutant versions of nucleic acids encoding an Bcl-G polypeptide by microinjection, retroviral infection or other means well known to those skilled in the art, into appropriate fertilized embryos to produce a transgenic animal, see, for example, Hogan et al., *Manipulating the Mouse Embryo: A Laboratory Manual* (Cold Spring Harbor Laboratory, (1986)). Transgenic animal model systems are useful for in vivo screening of compounds for identification of specific ligands, such as agonists or antagonists, which activate or inhibit a biological activity.

Also contemplated herein, is the use of homologous recombination of mutant or normal versions of Bcl-G genes with the native gene locus in transgenic animals, to alter the regulation of expression or the structure of Bcl-G polypeptides by replacing the endogeneous gene with a recombinant or mutated Bcl-G gene. Methods for producing a transgenic non-human mammal including a gene knock-out non-human mammal, are well known to those skilled in the art (see, Capecchi et al., *Science* 244:1288 (1989); Zimmer et al., *Nature* 338:150 (1989); Shastry, *Experentia,* 51:1028-1039 (1995); Shastry, *Mol. Cell. Biochem.,* 181:163-179 (1998); and U.S. Pat. No. 5,616,491, issued Apr. 1, 1997, U.S. Pat. No. 5,750,826, issued May 12, 1998, and U.S. Pat. No. 5,981, 830, issued Nov. 9, 1999).

Invention nucleic acids, oligonucleotides, including antisense, vectors containing invention nucleic acids, transformed host cells, polypeptides and combinations thereof, as well as antibodies of the present invention, can be used to screen compounds to determine whether a compound functions as a potential agonist or antagonist of invention polypeptides. These screening assays provide information regarding the function and activity of invention polypeptides, which can lead to the identification and design of compounds that are capable of specific interaction with one or more types of polypeptides, peptides or proteins.

Thus, the invention provides methods for identifying compounds which bind to Bcl-G polypeptides. The invention proteins can be employed in a competitive binding assay. Such an assay can accommodate the rapid screening of a large number of compounds to determine which compounds, if any, are capable of binding to Bcl-G polypeptides. Subsequently, more detailed assays can be carried out with those compounds found to bind, to further determine whether such compounds act as modulators, agonists or antagonists of invention Bcl-G polypeptides. Compounds that bind to and/or modulate invention Bcl-G polypeptides can be used to treat a variety of pathologies mediated by invention Bcl-G polypeptides.

Various binding assays to identify cellular proteins that interact with protein binding domains are known in the art and include, for example, yeast two-hybrid screening assays (see, for example, U.S. Pat. Nos. 5,283,173, 5,468,614 and 5,667, 973; Ausubel et al., supra, 1999; Luban et al., *Curr. Opin. Biotechnol.* 6:59-64 (1995)) and affinity column chromatography methods using cellular extracts. By synthesizing or expressing polypeptide fragments containing various Bcl-G sequences or deletions, the Bcl-G binding interface can be readily identified.

In another embodiment of the invention, there is provided a bioassay for identifying compounds which modulate the activity of invention Bcl-G polypeptides. According to this method, invention polypeptides are contacted with an "unknown" or test substance, for example, in the presence of a reporter gene construct responsive to a Bcl-G signaling pathway, the activity of the polypeptide is monitored subsequent to the contact with the "unknown" or test substance, and those substances which cause the reporter gene construct to be expressed are identified as functional ligands for Bcl-G polypeptides. Such reporter gene assays and systems are well known to those skilled in the art (Ausubel et al., supra, 1999).

In addition, a reporter gene constrict can be generated using the promoter region of Bcl-G and screened for compounds that increase or decrease Bcl-G gene promoter activity. Such compounds can also be used to alter Bcl-G expression.

In accordance with another embodiment of the present invention, transformed host cells that recombinantly express invention polypeptides can be contacted with a test compound, and the modulating effect(s) thereof can then be evaluated by comparing the Bcl-G-mediated response, for example, via reporter gene expression in the presence and absence of test compound, or by comparing the response of test cells or control cells, to the presence of the compound.

As used herein, a compound or a signal that "modulates the activity" of invention polypeptides refers to a compound or a signal that alters the activity of Bcl-G polypeptides so that the activity of the invention polypeptide is different in the presence of the compound or signal than in the absence of the compound or signal. In particular, such compounds or signals include agonists and antagonists. An agonist encompasses a compound or a signal that activates Bcl-G protein expression or biological activity. Alternatively, an antagonist includes a compound or signal that interferes with Bcl-G expression or biological activity. Typically, the effect of an antagonist is observed as a blocking of agonist-induced protein activation. Antagonists include competitive and non-competitive antagonists.

Assays to identify compounds that modulate Bcl-G polypeptide expression can involve detecting a change in Bcl-G polypeptide abundance in response to contacting the cell with a compound that modulates Bcl-G activity. Assays for detecting changes in polypeptide expression include, for example, immunoassays with Bcl-G-specific Bcl-G antibodies, such as immunoblotting, immunofluorescence, immunohistochemistry and immunoprecipitation assays, as described above.

As understood by those of skill in the art, assay methods for identifying compounds that modulate Bcl-G activity generally require comparison to a control. One type of a "control" is a cell or culture that is treated substantially the same as the test cell or test culture exposed to the compound, with the distinction that the "control" cell or culture is not exposed to the compound. Another type of "control" cell or culture can be a cell or culture that is identical to the test cells, with the exception that the "control" cells or culture do not express a Bcl-G polypeptide. Accordingly, the response of the transfected cell to a compound is compared to the response, or lack thereof, of the "control" cell or culture to the same compound under the same reaction conditions.

Methods for producing pluralities of compounds to use in screening for compounds that modulate the activity of a Bcl-G polypeptide, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.,* 2:363-371 (1998); Sofia, *Mol. Divers.* 3:75-94 (1998); Eichler et al., *Med. Res. Rev.* 15:481-496 (1995); and the like. Libraries containing large numbers of natural and synthetic compounds also can be obtained from commercial sources. Combinatorial libraries of molecules can be prepared using well known combinatorial chemistry methods (Gordon et al., *J. Med. Chem.* 37: 1233-1251 (1994); Gordon et al., *J. Med. Chem.* 37: 1385-1401 (1994); Gordon et al., *Acc. Chem. Res.* 29:144-154 (1996); Wilson and Czarnik, eds., *Combinatorial Chemistry: Synthesis and Application*, John Wiley & Sons, New York (1997)).

Compounds that modulate Bcl-G activity can be screened by the methods disclosed herein to identify compounds that modulate any biological activity or function of Bcl-G. For example, compounds can be identified that alter the interaction of Bcl-G with Bcl-2 family members. Additionally, compounds can be identified that modulate ion channel activity associated with Bcl-G. The formation of ion channels by Bcl-2 family members is one mechanism of inducing apoptosis in cells (Reed, supra, 1998). Therefore, compounds that modulate ion channel activity of Bcl-G can be used to alter apoptosis, thereby increasing or decreasing apoptotic activity of Bcl-G.

Another assay for screening of compounds that modulates the activity of Bcl-G is based on altering the phenotype of yeast by expressing Bcl-G. For example, expression of Bax in yeast confers a lethal phenotype (Matsuyama et al., *Mol. Cell.* 1:327-336 (1998)). A yeast that expresses Bcl-G can have a similar phenotype as Bax since the biological activity of Bcl-G is similar to Bax (Example III). Accordingly, a yeast strain expressing Bcl-G that confers a lethal phenotype can be screened for compounds that prevent cell death. In one embodiment, expression of Bcl-G can be inducible (Tao et al., *J. Biol. Chem.* 273:23704-23708 (1998), and the compounds can be screened when Bcl-G expression is induced. Bcl-G can also be co-expressed in yeast with other Bcl-2 family members having anti-apoptotic activity such as Bcl-2 or Bcl-$X_L$. For example, co-expression of Bax with Bcl-2 or Bcl-$X_L$ suppressed the lethal activity of Bax (Tao et al., supra, 1998). Similarly, co-expression of Bcl-G with an anti-apoptotic Bcl-2 family member such as Bcl-2 or Bcl-$X_L$ can be used to screen for compounds that antagonize the activity of the anti-apoptotic Bcl-2 family members and restore a lethal phenotype. Such compounds can function to inhibit binding of Bcl-G to anti-apoptotic Bcl-2 family members such as Bcl-2 or Bcl-$X_L$.

In yet another embodiment of the present invention, the activation of Bcl-G polypeptides can be modulated by contacting the polypeptides with an effective amount of at least one compound identified by the assays described herein. The invention also provides a method of identifying an effective agent that alters the association of a Bcl-G with a Bcl-G associated polypeptide (BAP). The method includes the steps of contacting the Bcl-G and the BAP polypeptide, under conditions that allow said Bcl-G and BAP polypeptide to associate, with a compound; and detecting the altered association of the Bcl-G and BAP polypeptide, thereby identifying a compound that is an effective agent for altering the association of Bcl-G with BAP. The compound can be, for example, a drug or polypeptide. A BAP can be, for example, Bcl-2 family member such as Bcl-2 or Bcl-$X_L$.

As disclosed herein, Bcl-G is a new member of the Bcl-2 family that has pro-apoptotic activity (see Example III). Therefore, modulation of Bcl-G activity can be advantageously used to modulate the level of apoptosis in a cell. For example, increasing the activity of Bcl-G can be used to promote apoptosis in a cell. Bcl-G activity can be increased, for example, by increasing the level of a Bcl-G polypeptide or functional fragment thereof. Increased levels of a Bcl-G polypeptide can be accomplished, for example, by delivering to a cell a nucleic acid encoding Bcl-G and expressing a Bcl-G polypeptide recombinantly or by delivering a Bcl-G polypeptide or functional fragment thereof directly to a target by the methods disclosed herein. Additionally, Bcl-G activity can be increased by using a modulatory agent that functions as an agonist. Promoting apoptosis by increasing Bcl-G activity or expression is useful, for example, in therapeutic applications such as the treatment of cancer.

As disclosed herein, decreases or loss of Bcl-G is associated with approximately 50% of prostate cancers, approximately 30% of ovarian cancers and approximately 30% of leukemias. Bcl-G can function as a tumor suppressor. Therefore, methods of administering a Bcl-G polypeptide either directly or using an encoded nucleic acid can be used to treat a cancer. Furthermore, many chemotherapeutic agents function through increasing apoptosis. Therefore, the invention additionally provides a method to enhance a chemotherapy by increasing Bcl-G activity or expression. Administering Bcl-G can thus be used to enhance the effect of standard chemotherapeutic agents.

Alternatively, modulation of Bcl-G activity can be advantageously used to decrease Bcl-G activity to decrease apoptosis. For example, Bcl-G activity or expression can be decreased by administering an anti-sense Bcl-G nucleic acid. In addition, an antagonist of Bcl-G activity can be identified by the methods disclosed herein and used to decrease Bcl-G activity. Decreasing Bcl-G activity can be used to inhibit apoptosis. Inhibiting apoptosis can be useful, for example, to treat disease ischemic. For example, decreasing Bcl-G activity with anti-sense nucleic acids or small molecule compounds can be used to treate stroke, heart attack, autoimmunity, trauma, neuron cell death, and inflammatory diseases, including Crohn's disease. For example, Bcl-G was identified in Crohn's disease patients (see Example I).

The invention further provides a method for modulating an activity mediated by a Bcl-G polypeptide by contacting the Bcl-G polypeptide with an effective, modulating amount of an agent that modulates Bcl-G activity. The Bcl-G activity can be, for example, apoptosis-inducing activity, binding to Bcl-2, or tumor suppresor activity. The invention additionally provides a method of modulating the level of apoptosis in a cell. The method includes the steps of introducing a nucleic acid molecule encoding a Bcl-G into the cell; and expressing the Bcl-G in the cell, wherein the expression of the Bcl-G modulates apoptosis in the cell.

The invention further provides a method of modulating the level of apoptosis in a cell by contacting the cell with a compound that effectively alters the association of Bcl-G with a Bcl-G-associated-protein in the cell, or that effectively alters the activity of a Bcl-G in the cell. Additionally provided by the invention is a method of modulating interactions between Bcl-G and Bcl-2 by contacting a Bcl-G polypeptide with the agent that inhibits or alters interactions between Bcl-G and Bcl-2.

As disclosed herein, Bcl-G is located on chromosome 12 in a region deleted in various cancers, including leukemia, prostate and ovarian cancer (Example IV). Therefore, methods using Bcl-G nucleic acids or antibodies can be used as a diagnostic for predisposition or progression of cancer, for example, leukemia, prostate or ovarian cancer. Changes in Bcl-G expression or activity can be correlated with patient survival or response to therapy, and a correlation can be used to monitor cancer progression or response to therapy.

The invention further provides a method of diagnosing a pathology characterized by an increased or decreased level of a Bcl-G in a subject. The method includes the steps of (a) obtaining a test sample from the subject; (b) contacting the sample with an agent that can bind the Bcl-G under suitable conditions, wherein the conditions allow specific binding of the agent to the Bcl-G; and (c) comparing the amount of the specific binding in the test sample with the amount of specific binding in a control sample, wherein an increased or decreased amount of the specific binding in the test sample as compared to the control sample is diagnostic of a pathology. The agent can be, for example, an anti-Bcl-G antibody, a Bcl-G-associated-protein (BAP), or a Bcl-G nucleic acid.

The invention also provides a method of diagnosing cancer or monitoring cancer therapy by contacting a test sample from a patient with a Bcl-G-specific antibody. The invention additionally provides a method of assessing prognosis of patients with cancer comprising contacting a test sample from a patient with a Bcl-G-specific antibody.

The invention additionally provides a method of diagnosing cancer or monitoring cancer therapy by contacting a test sample from a patient with a Bcl-G oligonucleotide. The invention further provides a method of assessing prognosis of patients with cancer by contacting a test sample from a patient with a Bcl-G oligonucleotide.

The methods of the invention for diagnosing cancer or monitoring cancer therapy using a Bcl-G-specific antibody or Bcl-G oligonucleotide or nucleic acid can be used, for example, to segregate patients into a high risk group or a low risk group for predicting risk of metastasis or risk of failure to respond to therapy. Therefore, the methods of the invention can be advantageously used to determine the risk of metastasis in a cancer patient or as a prognostic indicator of survival in a cancer patient. One of ordinary skill in the art would appreciate that the prognostic indicators of survival for cancer patients suffering from stage I cancer can be different from those for cancer patients suffering from stage IV cancer. For example, prognosis for stage I cancer patients can be oriented toward the likelihood of continued growth and/or metastasis of the cancer, whereas prognosis for stage IV cancer patients can be oriented toward the likely effectiveness of therapeutic methods for treating the cancer. Accordingly, the methods of the invention directed to measuring the level of or determining the presence of a Bcl-G polypeptide or encoding nucleic acid can be used advantageously as a prognostic indicator for the presence or progression of a cancer or response to therapy.

In accordance with another embodiment of the present invention, there are provided diagnostic systems, preferably in kit form, comprising at least one invention nucleic acid or antibody in a suitable packaging material. The diagnostic kits containing nucleic acids are derived from the Bcl-G-encoding nucleic acids described herein. In one embodiment, for example, the diagnostic nucleic acids are derived from any of SEQ ID NOS:1, 3 or 41 and can be oligonucleotides of the invention. Invention diagnostic systems are useful for assaying for the presence or absence of nucleic acid encoding Bcl-G in either genomic DNA or mRNA.

A suitable diagnostic system includes at least one invention nucleic acid or antibody, as a separately packaged chemical reagent(s) in an amount sufficient for at least one assay. For a diagnostic kit containing nucleic acid of the invention, the kit will generally contain two or more nucleic acids. When the diagnostic kit is to be used in PCR, the kit will contain at least two oligonucleotides that can serve as primers for PCR. Those of skill in the art can readily incorporate invention nucleic probes and/or primers or invention antibodies into kit form in combination with appropriate buffers and solutions for the practice of the invention methods as described herein. A kit containing a Bcl-G antibody can contain a reaction cocktail that provides the proper conditions for performing an assay, for example, an ELISA or other immunoassay, for determining the level of expression of a Bcl-G polypeptide in a sample, and can contain control samples that contain known amounts of a Bcl-G polypeptide and, if desired, a second antibody specific for the anti-Bcl-G antibody.

The contents of the kit of the invention, for example, Bcl-G nucleic acids or antibodies, are contained in packaging material, preferably to provide a sterile, contaminant-free environment. In addition, the packaging material contains instructions indicating how the materials within the kit can be employed both to detect the presence or absence of a particular Bcl-G sequence or Bcl-G polypeptide or to diagnose the presence of, or a predisposition for a condition associated with the presence or absence of Bcl-G such as cancer. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

It is understood that modifications which do not substantially affect the activity of the various embodiments of this invention are also provided within the definition of the invention provided herein. Accordingly, the following examples are intended to illustrate but not limit the present invention.

EXAMPLE I

Molecular Cloning of Bcl-G

This example describes the cloning of Bcl-G, a homologue of Bcl-2.

To clone the full length Bcl-G gene, oligonucleotide primers were designed based a short EST (GenBank Accession No. AW000827) from colonic mucosa of 3 patients with Crohn's disease found by searching a database for sequences similar to the BH2 and BH3 domains of Bcl-2 family proteins. The primers used were Primer 1 (5'GTACTTGGTGC-CAAAGCCCAGG-3'; SEQ ID NO:7) and Primer 2 (5'-GA-CATGATGTCTGGTGTAGTAGGCGAGG-3'; SEQ DI NO:8). The full length Bcl-G cDNA was cloned using SMART™RACE cDNA Amplification Kit (Clontech; Palo Alto Calif.) from human placental total RNA (Clontech) as template. The 5'-RACE products were sequenced with an automated sequencer.

Briefly, for cloning of Bcl-G cDNAs, TBLAST searches of the public databases using human Bcl-2 as a query sequence revealed a short EST (GenBank AW000827) from colonic mucosa of 3 patients with Crohn's disease which contains an open reading frame (ORF) encoding sequences similar to the BH2 domain of Bcl-2 family proteins. An -oligonucleotide primer (5'-GTACTTGGTGCCAAAGCCCAGG-3'; SEQ ID NO:7) was designed complementary to the EST sequence and used for 5'-RACE, employing the SMART™ RACE cDNA Amplification Kit (Clontech; Palo Alto Calif.) and human placental total RNA as template. The 5'-RACE products were subcloned into pCR2.1-TOPO vector using the TOPO™ TA Cloning kit (Invitrogen; Carlsbad Calif.), and their DNA sequence determined, revealing a complete open reading frame (ORF), with start codon within a favorable Kozak sequence context, preceded by a 5'-untranslated region (UTR) containing stop codons in all three reading-frames (submitted to Genbank). Two additional EST clones, AI478889 and AI240211, were identified by BLAST searches, corresponding to overlapping partial Bcl-G cDNAs which contained the 3'-UTR.

A short EST was identified during searches of the public databases, which when conceptually translated revealed a polypeptide sequence with similarity to the BH2 domain of Bcl-2 family proteins. Full-length cDNAs were obtained, revealing two potential transcripts containing open reading frames (ORF) for proteins of 327 and 252 amino-acids, respectively, which were termed Bcl-$G_L$ and Bcl-$G_S$ (FIG. 5A). The predicted Bcl-$G_L$ and Bcl-$G_S$ proteins are identical for the first 226 amino acids, then diverge thereafter. Comparison of the predicted amino acid sequences of Bcl-$G_L$ and Bcl-$G_S$ with Bcl-2 family proteins revealed the presence of a candidate BH3 domain (SEQ ID NO:9) in both Bcl-$G_L$ and Bcl-$G_S$ (FIG. 5A,B), and the presence of a BH2 domain (SEQ ID NO:18) in Bcl-$G_L$ but not in Bcl-$G_S$ (FIG. 5A, C).

Invention Bcl-G was found to exist in two forms, a long form, designated Bcl-$G_L$, and a shorter form, designated Bcl-$G_S$. The nucleotide sequence of Bcl-$G_L$ is shown in FIG. 1 (SEQ ID NO:1). The nucleotide sequence of the coding region of Bcl-$G_L$ cDNA and the encoded amino acid sequence (SEQ ID NO:3) are shown in FIG. 2. Bcl-$G_L$ was initially identified to contain a core BH3 domain ($^{216}$LKYS-GDQLE$^{224}$; SEQ ID NO:5) and a core BH2 domain ($^{307}$PWIQQHGGWE$^{316}$; SEQ ID NO:6).

The shorter form of Bcl-G, Bcl-$G_S$, is an apparent alternative splicing product of Bcl-G mRNA. The nucleotide sequence of Bcl-$G_S$ is shown in FIG. 3 (SEQ ID NO:3). The nucleotide sequence of the coding region of Bcl-$G_S$ cDNA and the encoded amino acid sequence (SEQ ID NO:4) are shown in FIG. 2. Bcl-$G_S$ contains only the BH3 domain ($^{216}$LKYSGDQLE$^{224}$).

These results demonstrate that a new member of the Bcl-2 family, Bcl-G, is expressed in human placenta and in the colonic mucosa of patients with Crohn's disease. Bcl-G exists in two forms, a long form, designated Bcl-$G_L$, which contains a BH2 and BH3 domain, and a short form, designated Bcl-$G_S$, which contains only a BH3 domain.

EXAMPLE II

Mapping of Bcl-G to Chromosome 12p12.3

This experiment describes chromosomal mapping of human Bcl-G.

To map the chromosomal location of Bcl-G, a search of the GenBank database was performed using BLAST (Altschul et al., *J. Mol. Biol.* 215:403-410 (1990); Altschul et al., *Nucleic Acids Res.* 25:3389-3402 (1997). A 190858 bp human 12p12 BAC chromosome sequence RPCI11-267J23 (GenBank accession no. AC007537) was found to contain the full length Bcl-G gene. The BAC also contains the LRP6 gene (exon 1 starts at 89963 bp). A 600 kb region between 12p12.3 to 12p13.1, flanked by D12S358 and ETV6/exon8, was previously defined to be frequently deleted in childhood acute lymphoblastic leukemia (ALL) and other solid tumor cells (Baens et al., (1999) *Genomics* 56:40-50 (1999); Hatta et al., *Br. J. Cancer* 75:1256-1262 (1997); Kibel et al., *Cancer Res.* 58:5652-5655 (1998); Baccichet et al., *Br. J. Haematol.* 99:107-114 (1997); Aissani et al., *Leuk. Lymphoma* 34:231-239). The loss of the region containing Bcl-G occurs in approximately 50% of prostate cancers, 30% of ovarian cancers, and 30% of leukemias.

The LRP6 gene is located in the region between 12p12.3 to 12p13.1. Using LRP6 as a marker for orientation, Bcl-G was located in this region. Exon 1 of Bcl-G starts at 40674 bp in the BAC and was deduced from novel DNA sequence data obtained from 5' RACE-based amplification of the full-length Bcl-G cDNA. The genomic structure of the Bcl-G gene is shown in FIG. 5. Bcl-$G_L$ has 6 exons, with the first codon non-coding, spreading across a 30 kb region in chromosome 12. Bcl-$G_S$ also has 6 exons, but a 153 bps sequence is inserted in front of exon 5 and contains a stop codon. The BH3 domain is located in exon 4 of both Bcl-$G_L$ and Bcl-$G_S$. The BH2 domain is located in exon 5 of Bcl-$G_L$. The Bcl-$G_L$ and Bcl-$G_S$ cDNAs can be accounted for by an alternative mRNA splicing mechanism in which different splice acceptor sites associated with exon 5 are employed, resulting in a change in the distal reading-frame (FIG. 5D).

Figure 6:
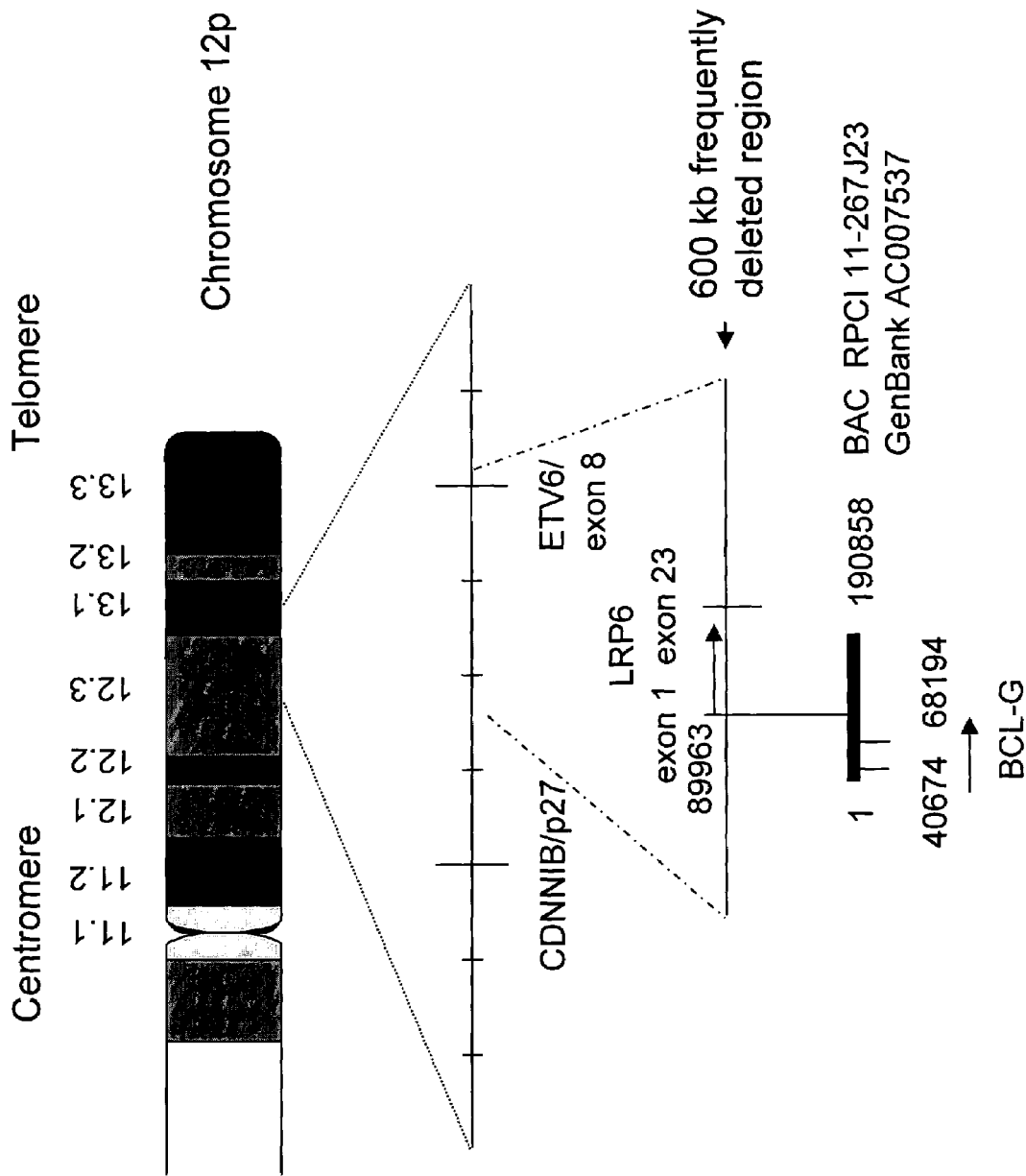
FIG. 6 shows mapping of Bcl-G to chromosome 12p12.3.

The chromosomal mapping of Bcl-G to chromosome 12p12.3 is shown in FIG. 6. Bcl-G is located in a 600 kb region that has been previously determined to be frequently deleted in childhood ALL and other solid tumors (Baens et al., supra, 1999). Therefore, Bcl-G is located in a region deleted in ALL and can function as a tumor suppressor or as a marker for tumor suppressor activity.

EXAMPLE III

Expression of Bcl-G

This example describes the expression of Bcl-G.

For generation of plasmids, cDNAs containing the ORFs of Bcl-$G_L$ and Bcl-$G_S$ without additional flanking sequences were generated by PCR using human placental cDNA as a template and the following primers:

5'-GGCTCGAGCGATGTGTAGCAC-CAGTGGGTGTGACC-3' (SEQ ID NO:27), sense for both Bcl-$G_L$ and Bcl-$G_S$;

5'-CCAAGCTTTAAGTCTACTTCTTCATGTGATATCCC-3' (SEQ ID NO:28), antisense for Bcl-$G_L$; and 5'-CCAAGCTTTAAAATGCAGGCCATCAAACC-3' (SEQ ID NO:29), antisense for Bcl-$G_S$. The resulting PCR products were digested with restriction endonucleases and subcloned into the Xho I and Hind III sites of pEGFP-Cl (Clontech). A mutant of Bcl-$G_S$ lacking the BH3 domain was created by a two-step PCR method, using the following primers: primer1,

5'-GGCTCGAGCGATGTGTAGCAC-CAGTGGGTGTGACC-3' (SEQ ID NO:30);

primer2, 5'-CCGGATCCGGCTAGTATTTGTTCTTCT-TCATCTTTC-3' (SEQ ID NO:31); primer3, 5'-CCG-GATCCGACACTGCCTTCATCCCCATTCCC-3' (SEQ ID NO:32); and primer4, 5'-CCAAGCTTTAAAATG-CAGGCCATCAAACC-3' (SEQ ID NO:33). The resulting PCR product was digested with XhoI/BamHI or with BamHI/HindIII respectively, and ligated into pEGFP-C1. Site-directed mutagenesis of Bcl-$G_S$ was performed to generate a L216E substitution mutation using the QuikChange™ Site-Directed Mutagenesis Kit (Stratagene) following manufacturer's procedure, with pEGFP-C1/Bcl-$G_S$ plasmid as DNA template, and the mutagenic primers: 5'-GCCAAAATTGTTGAGCTGGAGAAATAT-TCAGGAGATCAGTTGG-3' (SEQ ID NO:34) and

5'-CCAACTGATCTCCTGAATATTTCTC-CAGCTCAACAATTTTGGC-3' (SEQ ID NO:35).

For measurements of Bcl-G mRNAs, Bcl-G mRNAs were detected by either Northern blotting or Reverse-Transcriptase-Polymerase Chain Reaction (RT-PCR). For RT-PCR, multiple-tissue CDNA panels (Clontech) containing first-strand cDNA generated from 16 different tissues were employed. PCR was performed according to the manufacturer's protocol with following primers: (a) 5' primer for both Bcl-$G_S$ and Bcl-$G_L$, corresponding to exon 3, 5'-CT-GAGGGTCTCTCCTTCCAGCTCCAAGG-3' (SEQ ID NO:36); (b) 3' primer for Bcl-$G_L$, corresponding to exon 5, 5'-GGCCGTGACGTCTATTACAAGGGCAGCC-3' (SEQ ID NO:37); and 3' primer for Bcl-$G_S$, corresponding to an alternatively spliced segment of exon 5, 5'-CAAGG-GAATGGGGATGAAGGCAGTGTC-3' (SEQ ID NO:38). Human G3PDH expression was examined by PCR with the following primers: 5'-TGAAGGTCGGAGTCAACG- GATTTGGT-3' (SEQ ID NO:39)(sense); and 5'-CAT-GTGGGCCATGAGGTCCACCAC- 3' (SEQ ID NO:40)(antisense).

Figure 7:
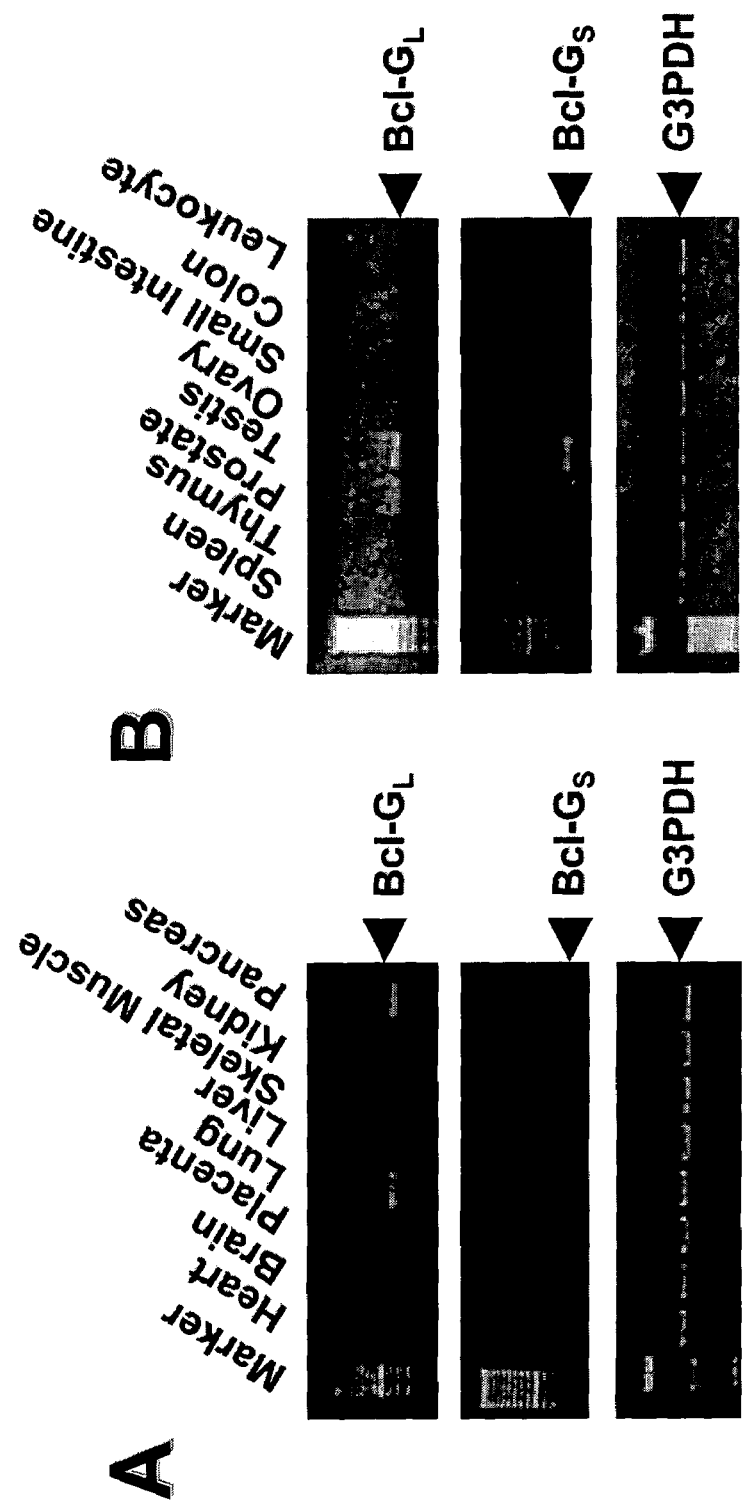
FIG. 7 shows expression of Bcl-G$_s$ and Bcl-G$_L$ in human tissues. The expression of transcripts encoding Bcl-G$_L$ or Bcl-G$_S$ was examined by RT-PCR. First-strand cDNA prepared using RNA samples from various adult human tissues was PCR amplified using primers specific for Bcl-G$_L$ and Bcl-G$_S$, based on differences in splice-acceptor utilization in exon 5. The primers flank an intron in both cases, thus excluding amplification due to contaminating genomic DNA. PCR products were size-fractionated in 2% agarose gels, stained with ethidium bromide, then photographed under UV-illumination.

For tissue-specific expression of Bcl-$G_L$ and Bcl-$G_S$ mRNAs, Northern blotting demonstrated the presence of ~2 kbp Bcl-G transcripts in several normal human tissues, but failed to resolve the mRNAs encoding Bcl-$G_L$ and Bcl-$G_S$. RT-PCR assays were therefore designed using primers specific for Bcl-$G_L$ and Bcl-$G_S$ sequences associated with exon 5. Bcl-$G_L$ mRNA was clearly detected in lung, pancreas, prostate and testis, with lower levels present in some other tissues (FIG. 7). In contrast, Bcl-$G_S$ mRNA was uniquely expressed in testis. RT-PCR amplification of a control mRNA, G3PDH, demonstrated loading of nearly equivalent amounts of mRNA from each tissue. The amplified bands corresponding to Bcl-$G_L$ and Bcl-$G_S$ were excised and sequenced, confirming the validity of the RT-PCR strategy.

EXAMPLE IV

Induction of Cell Death by Bcl-$G_S$

This experiment describes the induction of cell death by Bcl-$G_S$ in transfected PC-3 cells.

For cell culture, transfections, and apoptosis assay, 293T and Cos-7 cells were cultured in DMEM high glucose media (Irvine Scientific, Santa Ana, Calif.) containing 10% fetal bovine serum (FBS). PC-3 cells were cultured with RPMI 1640 media containing 10% FBS. Transfection of cells was performed using SuperFect (Qiagen, Chatsworth, Calif.). Both floating and adherent cells (after trypsinization) were collected 24 hrs after transfection, fixed, and stained using 4',6-diamidine-2'-phenylindole dihydrochloride (DAPI) for assessing apoptosis based on nuclear fragmentation and chromatin condensation (Xu & Reed, *Mol. Cell,* 1:337-346 (1998); Zhang et al., *Proc. Natl. Acad. Sci. (USA),* 97:2597-2602 (2000)).

To characterize a biological function of Bcl-G, a Bcl-$G_S$ construct was generated by cloning Bcl-$G_S$ cDNA into pcDNA3.1/Myc/His expression vector (Invitrogen; Carlsbad Calif.) at the Xho I/Hind III sites. The authenticity of the construct was confirmed by DNA sequencing.

For transfection experiments, various vectors were transfected into PC-3 cells: control vector pcDNA3.1/Myc/His; pcDNA3.1/Myc/His/Bcl-$G_S$ expressing Bcl-$G_S$; pRC/CMV/Bcl-2 expressing Bcl-2; and pRC/CMV/Bax expressing Bax. The vectors were transfected as follows: pcDNA3.1/Myc/His alone; pcDNA3.1/Myc/His/Bcl-$G_S$ alone; pcDNA3.1/Myc/His/Bcl-$G_S$+pRC/CMV/Bcl-2; pRC/CMV/Bax alone; or pRC/CMV/Bax+pRC/CMV/Bcl-2. One μg of each vector was combined with 0.2 μg pEGFP-N2 (Clontech), and the vectors were transiently transfected into PC-3 prostate cancer cells using SuperFect reagent (QIAGEN; Valencia Calif.), following the instructions of the manufacturer. At 24 hours after transfection, cells were examined under a fluorescent microscope. About 100 green fluorescent protein (GFP) positive (green color) cells were counted for each transfection. Cells that were detached with membrane blebbing and/or apoptotic bodies were recorded as dead cells. Results were averaged from three separate transfections.

Figure 8:
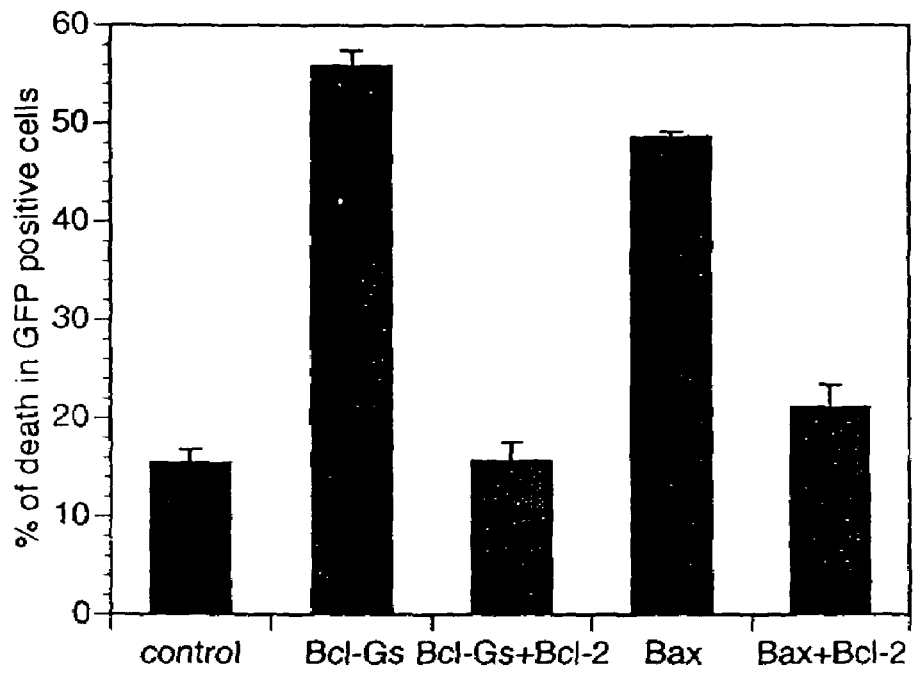
FIG. 8 shows the effect of Bcl-G$_S$ on cell death. PC-3 cells were transfected with pcDNA3.1/Myc/His (control), pcDNA3.1/Myc/His/Bcl-G$_S$ (Bcl-G$_S$), pcDNA3.1/Myc/His/Bcl-G$_S$+pRC/CMV/Bcl-2 (Bcl-G$_S$+Bcl-2), pRC/CMV/Bax (Bax), or pRC/CMV/Bax+pRC/CMV/Bcl-2 (Bax+Bcl-2). Cells were tested for cell death 24 hours after transfection.

As shown in FIG. 8, Bcl-$G_S$ induces cell death in PC-3 cells (compare "control" to "Bcl-$G_s$"). The induction of cell death by Bcl-$G_S$ was similar to Bax, which was used as a positive control based on its known pro-apoptotic activity (compare "Bcl-$G_S$" to "Bax"). The induction of cell death by Bcl-$G_S$ was completely inhibited when co-transfected with the anti-apoptotic Bcl-2 (see "Bcl-$G_S$+Bcl-2"). The inhibition of Bcl-$G_S$-induced cell death by Bcl-2 was similar to that seen with Bax (see "Bax+Bcl-2").

Figure 9:
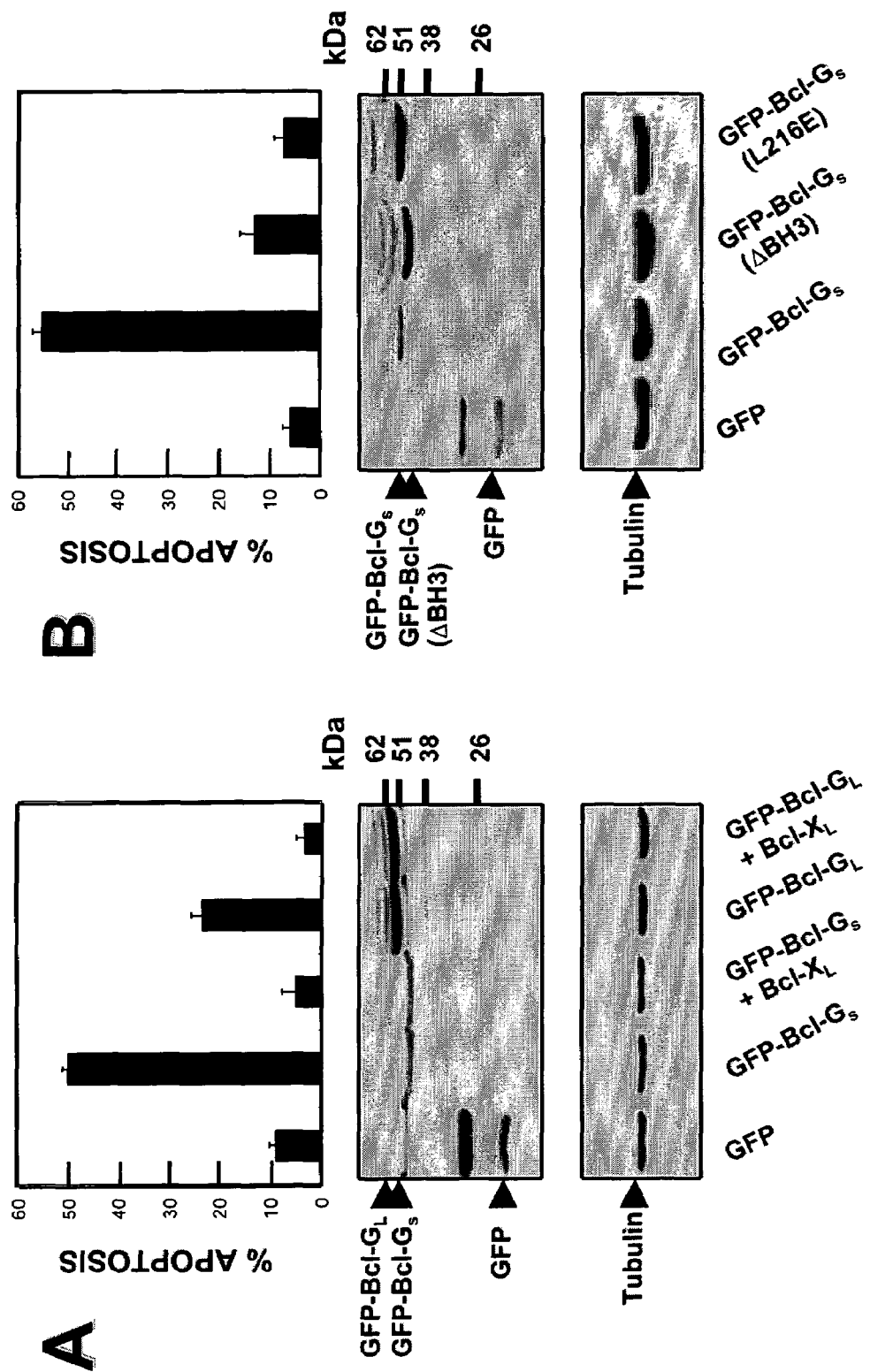
FIG. 9 shows induction of apoptosis by Bcl-G.

To assess the effects of Bcl-$G_L$ and further assess the effects of Bcl-$G_S$ on apoptosis, various cell lines, including Cos7, HEK293T, and PC3, were transiently transfected with plasmids encoding Bcl-$G_L$ or Bcl-$G_S$. For most experiments, Bcl-$G_L$ and Bcl-$G_S$ were expressed as GFP-fusions so that successfully transfected cells could be conveniently identified (FIG. 9A), but similar results were obtained when Flag-epitope tags were employed instead. Over-expression of the shorter Bcl-$G_S$ protein reproducibly induced striking increases in the percentage of cells undergoing apoptosis, as determined by DAPI staining (FIG. 9) and other methods. In contrast, Bcl-$G_L$ was more variable and less efficient at inducing apoptosis in these transient transfection assays. Immunoblot analysis of lysates from transfected cells demonstrated that the less potent effects of Bcl-$G_L$ could not be accounted for by lower levels of protein production (FIG. 9A). Indeed, Bcl-$G_L$ protein accumulated to levels ~10-fold higher in cells compared to Bcl-$G_S$, suggesting that Bcl-$G_S$ is a far more potent apoptosis-inducer. Analysis of the same blots with an anti-tubulin antibody confirm loading of essentially equivalent amounts of total protein for each sample, thus validating the results. In additional transfection experiments, Bcl-$G_L$ failed to demonstrate cytoprotective activity in side by side comparisons with Bcl-2 and Bcl-$X_L$.

EXAMPLE V

The BH3 Domain of Bcl-$G_S$ is Required for its Pro-apoptotic Activity

The Bcl-$G_S$ protein contains a BH3 domain, but lacks other regions of homology with Bcl-2 family proteins. Structural studies indicate that BH3 domains represent amphipathic α-helices, in which the hydrophobic surface of the α-helices of apoptosis-inducing BH3 peptides bind to a pocket on survival proteins such as Bcl-$X_L$ (Sattler et al., *Science,* 275: 983-986 (1997)). Therefore, the apoptosis-inducing activity of the wild-type Bcl-$G_S$ protein was compared with mutants lacking the BH3 domain (ΔBH3) or in which leucine 216 within the BH3 domain of Bcl-$G_S$ was chosen for mutation to charged glutamic acid, based on comparisons with previously described BH3 mutagenesis experiments demonstrating a critical requirement for the analogous leucine in other pro-apoptotic Bcl-2 family proteins (Wang et al., *Mol. Cell. Biol.,* 18:6083-6089 (1998); Kelekar et al., *Mol. Cell. Biol.,* 17:7040-7046 (1997)).

Wild-type Bcl-$G_S$ potently induced apoptosis when over-expressed in Cos-7, PC3, HEK293T and other cell lines, whereas Bcl-$G_S$ (ΔBH3) and Bcl-$G_S$ (L216E) did not (see FIG. 3B). Immunoblot analysis confirmed production of the Bcl-$G_S$ (ΔBH3) and Bcl-$G_S$ (L216E) proteins at levels exceeding the amounts of wild-type Bcl-$G_S$ protein. Therefore, the BH3 domain of Bcl-$G_S$ is critical for its pro-apoptotic activity.

EXAMPLE VI

Bcl-$G_S$ Associates with Bcl-$X_L$ in a BH3-dependent Manner

The pro-apoptotic activity of "BH3-only" members of the Bcl-2 family depends on their ability to dimerize with and suppress the activity of survival proteins such as Bcl-$X_L$ (reviewed in Kelekar & Thompson, *Trends Cell Biol.,* 8:324-

330 (1998)). It was, therefore, determined whether Bcl-$G_L$ and Bcl-$G_S$ are capable of associating with other Bcl-2 family proteins by co-immunoprecipitation assays.

For co-immunoprecipitations and immunoblotting, immunoblotting was performed as described previously (Xu and Reed, supra., (1998); Zhang et al., supra., (2000)). For co-immunoprecipitations, cells were cultured in 50 mM benzocarbonyl Valine Alanine Aspartate fluoromethyl-ketone (zVAD-fmk) to prevent apoptosis. Cells were suspended in lysis buffer (50 mM Tris-HCl, pH7.4; 150 mM NaCl; 20 mM EDTA; 50 mM NaF; 0.5% NP-40; 0.1 mM $Na_3VO_4$; 20 µg/ml Leupeptin; 20 µg/ml Aprotinin; 1 mM dithiothreitol (DTT); and 1 mM phenylmethylsulfonylfluoride (PMSF). Lysates (0.2 ml diluted into 1 ml final volume of lysis buffer) were cleared by incubation with 15 µl of protein G-Sepharose 4B (Zymed; South San Francisco Calif.) and then incubated with 15 µl of polyclonal anti-GFP antibody (Santa Cruz; Santa Cruz Calif.) and 15 µl of protein G at 4° C. overnight. Beads were then washed 4 times with 1.5 mls lysis buffer before boiling in Laemmli sample buffer and performing SDS-PAGE/immunoblotting.

Figure 10:
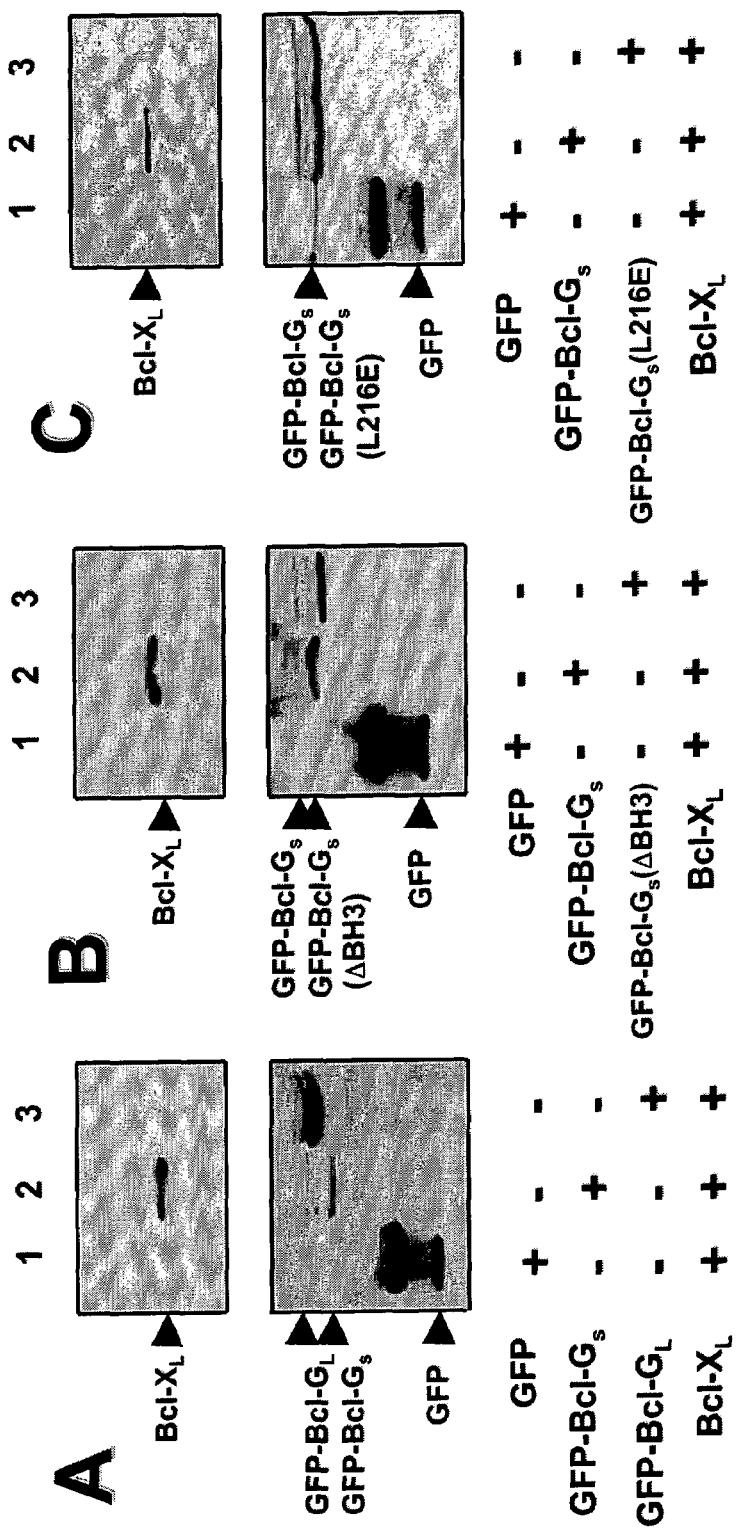
FIG. 10 shows interactions of Bcl-G$_S$ and Bcl-G$_L$ with Bcl-X$_L$. 293T cells were transiently transfected with plasmids encoding GFP, GFP-Bcl-G$_L$, GFP-Bcl-G$_S$, GFP-Bcl-G$_S$ (DBH3), or GFP-Bcl-G$_S$ (L218E). Cells were lysed 1 day later and immunoprecipitations were performed using anti-GFP antibody. Immune-complexes (prepared from 2 mg lysate) (top) and lysates (20 μg protein) (bottom) were subjected to SDS-PAGE/immunoblot analysis using anti-Bcl-X$_L$ (top) and anti-GFP (bottom) antibodies, respectively.

Bcl-$G_S$ association with the survival proteins Bcl-$X_L$ and Bcl-2 was readily detected by co-immunoprecipitation using lysates from transiently transfected cells, whereas no association with pro-apoptotic proteins Bax, Bak, Bid or Bad was observed (FIG. 10A). Interaction of Bcl-$G_S$ with Bcl-2 and Bcl-$X_L$, but not with Bax or Bak, was also confirmed by yeast two-hybrid assays. In contrast, association of the longer Bcl-$G_L$ protein with Bcl-2 or Bcl-$X_L$ was not easily detected by co-immunoprecipitation assays (FIG. 10A). With much longer x-ray film exposure times, however, small amounts of Bcl-$X_L$ were observed in association with Bcl-$G_L$ immunocomplexes, suggesting either low affinity binding of Bcl-$G_L$ to Bcl-$X_L$ or implying that only a small portion of total Bcl-$G_L$ proteins are competent to bind Bcl-$X_L$. The interaction of Bcl-$G_S$ with Bcl-$X_L$ was BH3-dependent, as determined by comparisons of wild-type Bcl-$G_S$ with the Bcl-$G_S$ (ΔBH3) and Bcl-$G_S$ (L216E) proteins (FIGS. 10B, C). Thus, the pro-apoptotic activity of Bcl-$G_S$ correlates with it ability to bind Bcl-$X_L$.

EXAMPLE VII

Bcl-$G_S$ is Associated with Cytosolic Organelles

Many Bcl-2 family proteins, such as Bcl-2, Bcl-$X_L$, and Bak, contain a hydrophobic stretch of amino-acids near their carboxyl-terminus that anchors them in intracellular membranes of mitochondria, endoplasmic reticulum, or nuclear envelope (reviewed in Reed, J. C., Nature, 387:773-776 (1997); Adams & Cory, Science, 281:1322-1326 (1998); Gross et al., Genes Dev., 13:1899-1911 (1999)). However, some pro-apoptotic Bcl-2 family proteins, such as Bax, Bid, and Bim, are found in the cytosol and must be induced to translocate to mitochondria and other organelles where the Bcl-2-family proteins to which they dimerize reside (Wolter et al., J. Cell Biol., 139:1281-1292 (1997); Puthalakath et al., Mol. Cell, 3:287-96 (1999); Li et al., Cell, 94:491-501 (1998); Luo et al., Cell, 94:481-490 (1998)).

The intracellular locations of the Bcl-$G_L$ and Bcl-$G_S$ protein was examined by confocal microscopy analysis of cells expressing GFP-tagged proteins. GFP-expressing cells were imaged by confocal microscopy using a Bio-Rad MRC 1024 instrument (Xu & Reed, supra. (1998); Zhang et al., supra. (2000); Zha et al., Mol. Cell. Biol., 16:6494-6508 (1996)). GFP-Bcl-$G_L$ protein was located diffusely throughout cells, similar to GFP control protein (FIG. 11A, B). In contrast, Bcl-$G_S$ was found in a punctate cytosolic pattern (FIG. 1C), suggestive of organelle association. Surprisingly, deletion of the BH3 domain from Bcl-$G_S$ did not disrupt the punctate distribution (FIG. 5D), indicating that other regions of the Bcl-$G_S$ protein are sufficient for subcellular targeting. Subcellular fractionation experiments confirmed these observations, demonstrating association of Bcl-$G_S$ and Bcl-$G_S$ (DB43) predominantly with organelle-containing heavy-membrane fractions, with scant amounts in the soluble cytosolic compartment.

EXAMPLE VIII

Loss of Heterozygosity (LOH) is Associated with Bcl-G in Ovarian Tissue

This example describes loss of heterozygosity (LOH) associated with Bcl-G in ovarian cancer tissue.

Ovarian cancer tissue samples were tested for SSCP for possible mutations in Bcl-G. No mutation was found in exon 1. However, about one third of the ovarian samples showed a possible LOH of Bcl-G. The LOH was observed as a change in band intensity using SSCP. The results were confirmed independently using PCR. The LOH samples are sequenced to determine specific mutations.

These results indicate that LOH is associated with Bcl-G in ovarian tissue and can be useful as a marker for ovarian cancer.

EXAMPLE IX

Cloning of Mouse Bcl-G

This example describes cloning of mouse Bcl-G.

The mouse Bcl-G was identified by searching GenBank. An EST clone (AA536718) was found to contain mouse Bcl-G. The EST was purchased from the American Type Culture Collection (ATCC; Manassas Va.) and sequenced to determine the complete sequence of mouse Bcl-G.

The nucleotide sequence of mouse Bcl-G cDNA is referenced as SEQ ID NO:41. The amino acid sequence of Bcl-G is referenced as SEQ ID NO:42.

PCR was used to isolate mouse Bcl-G from the purchased EST clone and clone it into EGFP-C1 vector. The primers used were MXSTA, 5'-GGGCTCGAGATGTGCAGCACCAGTGTGTATG-3' (SEQ ID NO:43); NHREV, 5'-CCAAGCTTTAAGTC-TACTTCTTCATGTGATATCCC-3' (SEQ ID NO:44).

In preliminary experiments, mouse Bcl-G was overexpressed in Cos-7 and 293T cells. In these preliminary experiments, apoptosis was not observed.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

What is claimed is:

1. A Bcl-G oligonucleotide, comprising between 15 and 300 contiguous nucleotides of SEQ ID NOS:1 or 3 or the anti-sense strand thereof.

2. An oligonucleotide according to claim 1, wherein said oligonucleotide is labeled with a detectable marker.

3. A kit for detecting the presence of a Bcl-G nucleic acid sequence comprising at least one oligonucleotide according to claim 2.

4. A method for identifying nucleic acids encoding a mammalian Bcl-G, comprising contacting a sample containing nucleic acids with one or more oligonucleotides according to claim 1, wherein said contacting is effected under high stringency hybridization conditions, and identifying a nucleic acid that hybridizes to said oligonucleotide.

5. A method of detecting a Bcl-G nucleic acid molecule in a sample, comprising contacting said sample with two or more Bcl-G oligonucleotides of claim 1, amplifying a nucleic acid molecule, and detecting said amplification.

6. The method of claim 5, wherein said amplification is performed using polymerase chain reaction.

7. Single stranded nucleic acid primers for amplification of a Bcl-G nucleic acid, wherein said primers each comprise between 15 and 300 contiguous nucleotides of SEQ ID NOS:1 or 3, or the antisense strand thereof.

8. An isolated nucleic acid encoding a Bcl-G polypeptide comprising a nucleotide sequence encoding a polypeptide having at least 90% identity to SEQ ID NO:2 or 4, or a functional fragment of said polypeptide, wherein said polypeptide has Bcl-G functional activity.

9. The isolated nucleic acid of claim 8, comprising a nucleotide sequence encoding a polypeptide having at least 95% identity to SEQ ID NO:2 or 4.

10. The isolated nucleic acid of claim 8, wherein the nucleotide sequence of said nucleic acid has at least 90% identity to the Bcl-G coding portion of SEQ ID NO:1 or 3.

11. The isolated nucleic acid of claim 10, wherein the nucleotide sequence of said nucleic acid has at least 95% identity to the Bcl-G coding portion of SEQ ID NO:1 or 3.

12. The isolated nucleic acid of claim 10, wherein the nucleotide sequence of said nucleic acid is degenerate with respect to SEQ ID NO:1 or 3.

13. An isolated nucleic acid encoding a Bcl-G polypeptide having an amino acid sequence set forth in SEQ ID NO:2 or 4.

14. The isolated nucleic acid of claim 13, wherein said nucleic acid is set forth in SEQ ID NO:1 or 3.

15. The nucleic acid of claim 13, wherein said nucleic acid is cDNA.

16. A vector containing the nucleic acid of claim 13.

17. Recombinant cells containing the nucleic acid of claim 13.

18. A method for expression of a Bcl-G polypeptide, said method comprising culturing cells of claim 17 under conditions suitable for expression of said Bcl-G.

19. An antisense-nucleic acid capable of specifically binding to mRNA encoded by said nucleic acid according to claim 13 wherein said antisense-nucleic acid comprises at least 15 nucleotides and inhibits expression of Bcl-G.

20. A composition comprising an amount of the antisense-nucleic acid according to claim 19 effective to inhibit expression of a human Bcl-G and an acceptable carrier capable of delivering Bcl-G to a cell.

21. The isolated nucleic acid of claim 8, comprising a nucleotide sequence encoding a functional fragment of SEQ ID NO:2 or 4.

22. The isolated nucleic acid of claim 21, which encodes a functional fragment comprising an amino acid sequence selected from SEQ ID NOS:5, 6, 9 or 18.

23. The isolated nucleic acid of claim 21, which encodes a functional fragment consisting of an amino acid sequence selected from SEQ ID NOS:5, 6, 9or 18.

24. The nucleic acid of claim 8, wherein said nucleic acid is cDNA.

25. A vector containing the nucleic acid of claim 8.

26. Recombinant cells containing the nucleic acid of claim 8.

27. A method for expression of a Bcl-G polypeptide, said method comprising culturing cells of claim 26, under conditions suitable for expression of said Bcl-G.

28. An antisense-nucleic acid capable of specifically binding to mRNA encoded by said nucleic acid according to claim 8 wherein said antisense-nucleic acid comprises at least 15 nucleotides and inhibits expression of Bcl-G.

29. A composition comprising an amount of the antisense-nucleic acid according to claim 28 effective to inhibit expression of a human Bcl-G and an acceptable carrier capable of delivering Bcl-G to a cell.

30. The oligonucleotide of claim 1, wherein the sequence is SEQ ID NO:1.

31. The oligonucleotide of claim 1, wherein the sequence is SEQ ID NO:3.

32. The nucleic acid primers of claim 7, wherein the sequence is SEQ ID NO:1.

33. The nucleic acid primers of claim 7, wherein the sequence is SEQ ID NO:3.

34. The nucleic acid of claim 8, wherein the sequence is SEQ ID NO:2.

35. The nucleic acid of claim 8, wherein the sequence is SEQ ID NO:4.

36. The nucleic acid of claim 9, wherein the sequence is SEQ ID NO:2.

37. The nucleic acid of claim 9, wherein the sequence is SEQ ID NO:4.

38. The nucleic acid of claim 10, wherein the sequence is SEQ ID NO:1.

39. The nucleic acid of claim 10, wherein the sequence is SEQ ID NO:3.

40. The nucleic acid of claim 11, wherein the sequence is SEQ ID NO:1.

41. The nucleic acid of claim 11, wherein the sequence is SEQ ID NO:3.

42. The nucleic acid of claim 12, wherein the sequence is SEQ ID NO:1.

43. The nucleic acid of claim 12, wherein the sequence is SEQ ID NO:3.

44. The nucleic acid of claim 13, wherein the sequence is SEQ ID NO:2.

45. The nucleic acid of claim 13, wherein the sequence is SEQ ID NO:4.

46. The nucleic acid of claim 14, wherein the sequence is SEQ ID NO:1.

47. The nucleic acid of claim 14, wherein the sequence is SEQ ID NO:3.

48. The antisense-nucleic acid of claim 19, wherein the sequence is SEQ ID NO:2.

49. The antisense-nucleic acid of claim 19, wherein the sequence is SEQ ID NO:4.

50. The composition of claim 20, wherein the sequence is SEQ ID NO:2.

51. The composition of claim 20, wherein the sequence is SEQ ID NO:4.

52. The nucleic acid of claim 21, wherein the sequence is SEQ ID NO:2.

53. The nucleic acid of claim 21, wherein the sequence is SEQ ID NO:4.

54. The nucleic acid of claim 22, wherein the sequence is SEQ ID NO:5.

55. The nucleic acid of claim 22, wherein the sequence is SEQ ID NO:6.

56. The nucleic acid of claim 22, wherein the sequence is SEQ ID NO:9.

57. The nucleic acid of claim 22, wherein the sequence is SEQ ID NO:18.

58. The nucleic acid of claim 23, wherein the sequence is SEQ ID NO:5.

59. The nucleic acid of claim 23, wherein the sequence is SEQ ID NO:6.

60. The nucleic acid of claim 23, wherein the sequence is SEQ ID NO:9.

61. The nucleic acid of claim 23, wherein the sequence is SEQ ID NO:18.

62. The antisense-nucleic acid of claim 28, wherein the sequence is SEQ ID NO:2.

63. The antisense-nucleic acid of claim 28, wherein the sequence is SEQ ID NO:4.

64. The composition of claim 29, wherein the sequence is SEQ ID NO:2.

65. The composition of claim 29, wherein the sequence is SEQ ID NO:4.

* * * * *

UNITED STATES PATENT AND TRADEMARK OFFICE
CERTIFICATE OF CORRECTION

| | | |
|---|---|---|
| PATENT NO. | : 7,638,324 B2 | Page 1 of 1 |
| APPLICATION NO. | : 09/738396 | |
| DATED | : December 29, 2009 | |
| INVENTOR(S) | : Reed et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 435 days.

Signed and Sealed this

Twenty-first Day of December, 2010

David J. Kappos
*Director of the United States Patent and Trademark Office*